United States Patent
Kim et al.

(10) Patent No.: US 11,382,937 B2
(45) Date of Patent: Jul. 12, 2022

(54) **PROTEINS DERIVED FROM *STREPTOCOCCUS PYOGENES* BACTERIA AND USE THEREOF**

(71) Applicant: MD HEALTHCARE INC., Seoul (KR)

(72) Inventors: Yoon-Keun Kim, Paji-Si (KR); Jae Gyu Kim, Seoul (KR); Tae Seop Shin, Seoul (KR)

(73) Assignee: MD HEALTHCARE INC., Seoul (KR)

( * ) Notice: Subject to any disclaimer, the term of this patent is extended or adjusted under 35 U.S.C. 154(b) by 0 days.

(21) Appl. No.: 17/024,046

(22) Filed: Sep. 17, 2020

(65) Prior Publication Data
US 2021/0000884 A1   Jan. 7, 2021

Related U.S. Application Data

(63) Continuation of application No. PCT/KR2020/005420, filed on Apr. 24, 2020.

(30) Foreign Application Priority Data

Apr. 26, 2019   (KR) .................. 10-2019-0049284

(51) Int. Cl.
| | | |
|---|---|---|
| A61K 39/00 | (2006.01) |
| A61K 35/74 | (2015.01) |
| A61P 35/00 | (2006.01) |
| A61K 8/99 | (2017.01) |
| A61P 29/00 | (2006.01) |
| A61K 38/16 | (2006.01) |
| A61P 3/00 | (2006.01) |

(52) U.S. Cl.
CPC ............ *A61K 35/74* (2013.01); *A61K 8/99* (2013.01); *A61K 38/164* (2013.01); *A61P 3/00* (2018.01); *A61P 29/00* (2018.01); *A61P 35/00* (2018.01)

(58) Field of Classification Search
CPC ...................................................... A61K 35/74
See application file for complete search history.

(56) References Cited

U.S. PATENT DOCUMENTS

| 4,328,218 | A | | 5/1982 | Sotomura et al. |
| 5,559,211 | A | * | 9/1996 | Kumagai ............... A61P 31/00 530/350 |
| 7,253,333 | B2 | * | 8/2007 | Tanaka ............... A01K 67/0339 800/10 |
| 2006/0094649 | A1 | * | 5/2006 | Keogh .................. C07K 14/71 424/185.1 |

FOREIGN PATENT DOCUMENTS

| KR | 10-0169982 B1 | 2/1999 |
| KR | 10-2009-0122940 A | 12/2009 |
| KR | 10-1478089 B1 | 12/2014 |
| KR | 10-1670317 B1 | 10/2016 |
| WO | WO-2015157820 A1 * | 10/2015 ........... C07K 14/315 |

OTHER PUBLICATIONS

Langer et al. (American Journal of Obstetrics & Gynecology vol. 218, No. 6, pp. 581-589) (Year: 2018).*
Pollard et al (Nature Metabolism vol. 1, No. 3, pp. 340-349) (Year: 2019).*
Ugai et al (Cancer Gene Therapy vol. 10, pp. 187-192) (Year: 2003).*
Edwards et al (Journal of Infectious Diseases vol. 192, pp. 783-790) (Year: 2005).*
Coussens et al (Nature vol. 420, (6917) pp. 860-867) (Year: 2002).*
Lukasiewicz et al., "Microorganisms in the Treatment of Cancer: Advantages and Limitations", Hindawi, Journal of Immunology Research, 2018, vol. 2018, Article ID 2397808, 8 pages.
Pothiwala et al., "Metabolic Syndrome and Cancer", Metabolic Syndrome and Related Disorders, 2009, vol. 7, No. 4, pp. 279-288.

* cited by examiner

*Primary Examiner* — Albert M Navarro
(74) *Attorney, Agent, or Firm* — Vorys, Sater, Seymour and Pease LLP; Mih Suhn Koh

(57) ABSTRACT

Provided is a pharmaceutical composition for the prevention, alleviation, or treatment of inflammatory diseases, metabolic diseases, and cancer, comprising a *Streptococcus pyogenes* culture broth or a protein isolated from the culture broth as an active ingredient. The inventors of the presently claimed subject matter confirmed that, when administered to inflammatory disease, metabolic disease, and cancer models, a *Streptococcus pyogenes* culture broth or a protein isolated from the culture broth exhibited anti-inflammatory, anti-obesity, liver function-improving, and anticancer effects, and thus the *Streptococcus pyogenes* culture broth or the protein isolated from the culture broth according to the presently claimed subject matter can be effectively used to develop a drug, a health functional food, an inhalant, a cosmetic composition, or the like for preventing inflammatory diseases, metabolic diseases, and cancer, or alleviating or treating symptoms thereof.

5 Claims, 25 Drawing Sheets

FIG. 10A

| Score | Weight loss (%) | Stool consistency | Hematochezia |
|---|---|---|---|
| 0 | None | Normal | Absence |
| 1 | 0-10 | | |
| 2 | 11-15 | Loose stool | |
| 3 | 16-20 | | |
| 4 | >20 | Diarrhea | Presence |

FIG. 10B

| Day | | 0 | 1 | 2 | 3 | 4 | 5 | 6 | 7 | 8 |
|---|---|---|---|---|---|---|---|---|---|---|
| PBS | Weight loss | 0 | 0 | 0 | 0 | 0 | 0 | 0 | 0 | 0 |
| | Stool consistency | 0 | 0 | 0 | 0 | 0 | 0 | 0 | 0 | 0 |
| | hematochezia | 0 | 0 | 0 | 0 | 0 | 0 | 0 | 0 | 0 |
| DSS | Weight loss | 0 | 0 | 0 | 0 | 0 | 0 | 1 | 2 | 3 |
| | Stool consistency | 0 | 0 | 0 | 0 | 0 | 0 | 2 | 3 | 3 |
| | hematochezia | 0 | 0 | 0 | 0 | 1 | 3 | 3 | 4 | 5 |
| DSS+SP CM>100 kDa | Weight loss | 0 | 0 | 0 | 0 | 0 | 0 | 0 | 1 | 1.5 |
| | Stool consistency | 0 | 0 | 0 | 0 | 0 | 0 | 0 | 1 | 2 |
| | hematochezia | 0 | 0 | 0 | 0 | 0 | 0 | 1 | 1 | 3 |

PROTEINS DERIVED FROM *STREPTOCOCCUS PYOGENES* BACTERIA AND USE THEREOF

CROSS-REFERENCE TO RELATED APPLICATIONS

This application is a Continuation of PCT/KR2020/005420, filed Apr. 24, 2020, which claims the benefit of priority from Korean Patent Application No. 10-2019-0049284, filed Apr. 26, 2019 and Korean Patent Application No. 10-2020-0046639 filed Apr. 17, 2020, the contents of each of which are incorporated herein by reference in its entirety.

TECHNICAL FIELD

The present invention relates to proteins derived from *Streptococcus pyogenes* bacteria and a use thereof, and more particularly to a composition for preventing, alleviating, or treating inflammatory diseases, metabolic diseases, and cancer using a *Streptococcus pyogenes* bacteria culture broth or a protein isolated from the culture broth.

This application claims priority to and the benefit of Korean Patent Application Nos. 10-2019-0049284 and 10-2020-0046639 filed in the Korean Intellectual Property Office on Apr. 26, 2019 and Apr. 17, 2020, respectively, and all the contents disclosed in the specification and drawings of the applications are incorporated in this application.

BACKGROUND ART

Neutrophils are the most abundant white blood cells in mammals and play a vital role in innate immune responses such as a response to bacterial infection. Interleukin-8 (hereinafter referred to as IL-8) is a cytokine that is secreted from inflammatory cells, epithelial cells, vascular endothelial cells, and the like and causes neutrophil inflammation, and the secretion of IL-8 is increased by oxidative stress, which causes another oxidative stress, thereby amplifying an inflammatory response. IL-8 has been reported to be closely related with not only diseases characterized by neutrophil inflammation, but also metabolic diseases such as obesity, diabetes, and non-alcoholic hepatitis, cancer, and mental diseases such as depression and schizophrenia.

Bacteria belonging to the genus *Streptococcus* are anaerobic gram-positive bacteria that symbiotically live in the human body such as the oral cavity and vagina, secrete lactic acid in a fermentation process, and include 50 or more species. Among these, *Streptococcus pyogenes* is an alpha-hemolytic streptococcus bacterium present in the oral cavity, and is sometimes known to cause infective endocarditis.

While numerous inventions (KR 10-1478089, KR 10-1670317, and the like) which relate to treatment of inflammatory diseases by inhibiting the secretion of cytokines, there are no cases in which *Streptococcus pyogenes* culture broths or proteins isolated therefrom are used for the prevention or treatment of inflammatory diseases.

DISCLOSURE

Technical Problem

The inventors of the present invention isolated a protein from a culture broth obtained by culturing a *Streptococcus pyogenes* strain, and experimentally confirmed that the protein effectively inhibited the expression of inflammatory cytokines, and thus completed the present invention based on these findings.

Therefore, an object of the present invention is to provide a pharmaceutical composition for preventing or treating one or more selected from the group consisting of an inflammatory disease, a metabolic disease, and cancer, comprising a *Streptococcus pyogenes* culture broth or a protein isolated from the culture broth as an active ingredient.

Another object of the present invention is to provide a food composition for preventing or alleviating one or more selected from the group consisting of an inflammatory disease, a metabolic disease, and cancer, comprising a *Streptococcus pyogenes* culture broth or a protein isolated from the culture broth as an active ingredient.

Another object of the present invention is to provide an inhalant composition for preventing or alleviating a respiratory inflammatory disease, comprising a *Streptococcus pyogenes* culture broth or a protein isolated from the culture broth as an active ingredient.

Another object of the present invention is to provide a cosmetic composition for preventing or alleviating an inflammatory skin disease, comprising a *Streptococcus pyogenes* culture broth or a protein isolated from the culture broth as an active ingredient.

However, a technical problem to be achieved by the present invention is not limited to the aforementioned problems, and the other problems that are not mentioned may be clearly understood by a person skilled in the art from the following description.

Technical Solution

To achieve the object of the present invention as described above, the present invention provides a composition for preventing, treating, or alleviating one or more selected from the group consisting of an inflammatory disease, a metabolic disease, and cancer, comprising a *Streptococcus pyogenes* culture broth or a protein isolated from the culture broth as an active ingredient.

The composition may comprise a pharmaceutical composition, a food composition, an inhalant composition, or a cosmetic composition. In addition, the food composition may be a health functional food composition.

In addition, the present invention provides an inhalant composition for preventing or alleviating a respiratory inflammatory disease, comprising a *Streptococcus pyogenes* culture broth or a protein isolated from the culture broth as an active ingredient.

In addition, the present invention provides a cosmetic composition for preventing or alleviating an inflammatory skin disease, comprising a *Streptococcus pyogenes* culture broth or a protein isolated from the culture broth as an active ingredient.

In one embodiment of the present invention, the protein may be isolated from a *Streptococcus pyogenes* culture broth.

In another embodiment of the present invention, the protein may have a molecular weight of 100 kDa or more.

In another embodiment of the present invention, the composition according to the present invention may inhibit an inflammatory cytokine.

In another embodiment of the present invention, the composition may inhibit an inflammatory cytokine caused by *Helicobacter pylori*- or *E. coli*-derived extracellular vesicles.

In another embodiment of the present invention, the inflammatory cytokine may be interleukin-8.

In another embodiment of the present invention, the cancer may be one or more selected from the group consisting of lung cancer, laryngeal cancer, oral cancer, gastric cancer, colon-rectal cancer, liver cancer, cholangiocarcinoma, pancreatic cancer, breast cancer, ovarian cancer, cervical cancer, kidney cancer, bladder cancer, prostate cancer, brain tumors, leukemia, and lymphoma, but the present invention is not limited thereto.

In another embodiment of the present invention, the inflammatory disease may be one or more selected from the group consisting of: respiratory diseases comprising rhinitis, asthma, and chronic obstructive pulmonary disease; inflammatory diseases in the oral cavity, comprising periodontitis; digestive diseases comprising gastritis and inflammatory colitis; skin diseases comprising atopic dermatitis, psoriasis, and acne; arteriosclerosis and complications thereof; chronic hepatitis and liver cirrhosis; joint diseases comprising rheumatoid arthritis and osteoarthritis; and cancer caused by inflammation, but the present invention is not limited thereto.

In another embodiment of the present invention, the metabolic disease may be one or more selected from the group consisting of obesity, fatty liver, liver cirrhosis, liver ischemia, a liver abscess, hyperlipidemia, hypercholesterolemia, diabetes, dyslipidemia, atherosclerosis, coronary artery disease, alcoholic fatty hepatitis, non-alcoholic steatohepatitis, and stroke, but the present invention is not limited thereto.

In another embodiment of the present invention, the respiratory inflammatory disease may be one or more selected from the group consisting of a cold, pneumonia, pulmonary emphysema, lung fibrosis, acute rhinitis, chronic rhinitis, sinusitis, allergic rhinitis, acute bronchitis, chronic bronchitis, asthma, and chronic obstructive pulmonary disease (COPD), but the present invention is not limited thereto.

In another embodiment of the present invention, the inflammatory skin disease may be one or more selected from the group consisting of skin inflammation, psoriasis, lupus erythematous, dandruff, acute/chronic eczema, contact dermatitis, atopic dermatitis, seborrheic dermatitis, lichen simplex chronicus, intertrigo, exfoliative dermatitis, papular urticaria, solar dermatitis, and acne, but the present invention is not limited thereto.

The present invention also provides a method of preventing or treating one or more diseases selected from the group consisting of an inflammatory disease, a metabolic disease, and cancer, the method comprising administering the *Streptococcus pyogenes* culture broth or a protein isolated from the culture broth to a subject.

The present invention also provides a use of the *Streptococcus pyogenes* culture broth or a protein isolated from the culture broth for treating one or more diseases selected from the group consisting of an inflammatory disease, a metabolic disease, and cancer.

The present invention also provides a use of the *Streptococcus pyogenes* culture broth or a protein isolated from the culture broth for preparing a medicament for the treatment of one or more selected from the group consisting of an inflammatory disease, a metabolic disease, and cancer.

Advantageous Effects

The inventors of the present invention confirmed the anti-inflammatory effect of a *Streptococcus pyogenes* culture broth or a protein isolated from the culture broth when an inflammatory disease model was treated therewith, and thus the *Streptococcus pyogenes* culture broth or protein isolated therefrom according to the present invention can be effectively used to develop a drug, a health functional food, an inhalant, a cosmetic, or the like for the prevention of inflammatory diseases, metabolic diseases, and cancer and the alleviation or treatment of symptoms.

DESCRIPTION OF DRAWINGS

FIG. 10A illustrates criteria for evaluating, as a disease activity index (DAI) score, the weight change, stool properties, and degree of hematochezia of mice, in a dextran sulfate sodium (DSS)-induced colitis (DSS-colitis) mouse model.

FIG. 10B illustrates the results of evaluating, as a disease activity index, the efficacy of a *Streptococcus pyogenes* culture broth (SP CM>100 kDa) in a dextran sulfate sodium (DSS)-induced colitis (DSS-colitis) mouse model in accordance with the criteria of FIG. 10A.

BEST MODE

Figure 1:
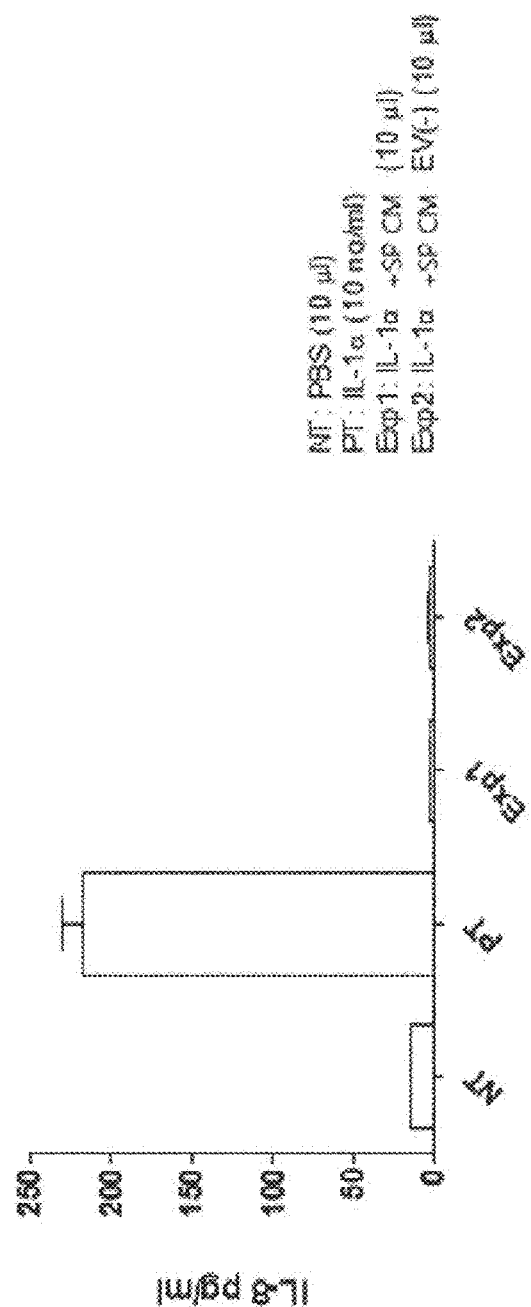
FIG. 1 illustrates the results of evaluating the efficacy of a *Streptococcus pyogenes* culture broth that inhibits the expression of the inflammatory cytokine IL-8, which is induced by IL-1α (10 ng/ml), in gastric epithelial cell lines (AGS and ATCC CRL-1739).

The inventors of the present invention confirmed that a *Streptococcus pyogenes*-derived culture broth and a protein isolated from the culture broth inhibited the expression of an inflammatory cytokine and had a therapeutic effect in inflammatory disease, metabolic disease, and cancer models, and thus completed the present invention based on these findings.

In one embodiment of the present invention, it was confirmed that, in the *Streptococcus pyogenes* culture broth, the supernatant, which is water-soluble, had an effect of inhibiting the expression of the inflammatory cytokine IL-8 (see Example 1), and particularly, it was confirmed that a water-soluble component having a molecular weight of 100 kDa or more inhibited the expression of the inflammatory cytokine IL-8 (see Example 2).

In other embodiments of the present invention, it was confirmed that the active ingredient that inhibits the expression of IL-8 is a protein component that is susceptible to heat (see Example 3), and it was confirmed that the *Streptococcus pyogenes*-derived protein had an effect of inhibiting the expression of the inflammatory cytokine IL-8, which is caused by *Helicobacter pylori*- or *E. coli*-derived extracellular vesicles (see Examples 4 and 5).

In other embodiments of the present invention, it was confirmed that the *Streptococcus pyogenes*-derived protein having a molecular weight of 100 kDa inhibited the expression of IL-8 in a concentration-dependent manner (see Example 6), and it was confirmed that the *Streptococcus pyogenes*-derived protein had an anti-inflammatory effect in a gastritis or colitis mouse model (see Examples 7 and 8).

In another embodiment of the present invention, it was confirmed that the *Streptococcus pyogenes*-derived protein had an anticancer effect in a cancer model (see Example 9).

In another embodiment of the present invention, it was confirmed that the *Streptococcus pyogenes*-derived protein had anti-obesity and anti-hepatitis effects in a metabolic disease model (see Example 10).

From the results of examples of the present invention, it was confirmed that the *Streptococcus pyogenes*-derived protein according to the present invention exhibited anti-inflammatory, anti-obesity, liver function protective, and anti-cancer effects, and thus the protein may be used for the prevention, alleviation, or treatment of inflammatory diseases, metabolic diseases, and cancer.

Thus, the present invention provides a pharmaceutical composition for preventing or treating one or more selected from the group consisting of an inflammatory disease, a metabolic disease, and cancer, comprising a *Streptococcus pyogenes* culture broth or a protein isolated from the culture broth as an active ingredient.

As used herein, the term "culture broth" refers to a culture broth itself obtained by culturing *Streptococcus pyogenes* bacteria according to the present invention in a suitable liquid medium, a filtrate (a filtered solution or a centrifuged supernatant) obtained by filtering or centrifuging the culture broth and removing the strain, a cell lysate obtained by ultrasonically treating the culture broth or treating the culture broth with lysozyme, or the like, preferably a supernatant after centrifugation, but the present invention is not limited thereto. In addition, the culture broth may include both a concentrate of the culture broth and a dried product of the culture broth. In the present invention, the culture broth may be a culture broth from which extracellular vesicles are removed.

The protein of the present invention may be separated and purified in the following order:
 a) centrifuging a liquid medium containing *Streptococcus pyogenes* to obtain a supernatant;
 b) filtering the supernatant; and
 c) isolating a protein from the filtered supernatant.

As used herein, the term "inflammatory disease" refers to a disease caused by serial bioreactions occurring due to a direct response of a humoral mediator constituting the immune system or stimulation of a local or systemic effector system, and the inflammatory disease may comprise, for example, one or more selected from the group consisting of: respiratory diseases comprising rhinitis, asthma, and chronic obstructive pulmonary disease; inflammatory diseases in the oral cavity, comprising periodontitis; digestive diseases comprising gastritis and inflammatory colitis; skin diseases comprising atopic dermatitis, psoriasis, and acne; arteriosclerosis and complications thereof; chronic hepatitis and liver cirrhosis; joint diseases comprising rheumatoid arthritis and osteoarthritis; and cancer caused by inflammation, but the present invention is not limited thereto.

The inflammatory disease of the present invention may be, for example, selected from the group consisting of an infectious inflammatory disease, cancer, an inflammatory skin disease, inflammatory bowel diseases such as Crohn's disease and ulcerative colitis, peritonitis, osteomyelitis, cellulitis, meningitis, encephalitis, pancreatitis, trauma-induced shock, bronchial asthma, allergic rhinitis, cystic fibrosis, stroke, acute bronchitis, chronic bronchitis, acute bronchiolitis, chronic bronchiolitis, osteoarthritis, gout, spondyloarthropathy, ankylosing spondylitis, Reiter's syndrome, psoriatic arthropathy, bowel disease spondylitis, juvenile arthropathy, juvenile ankylosing spondylitis, reactive arthropathy, infectious arthritis, post-infectious arthritis, gonococcal arthritis, tuberculous arthritis, viral arthritis, mycotic arthritis, syphilitic arthritis, Lyme disease, vasculitis syndrome-related arthritis, polyarteritis nodosa, hypersensitivity vasculitis, Lou Gehrig's granulomatosis, polymyalgia rheumatica, joint cell arteritis, calcium pyrophosphate deposition arthropathy, pseudo gout, non-articular rheumatism, bursitis, tendovaginitis, epicondylitis (tennis elbow), neuropathic joint disease (or called "Charcot joint"), hemarthrosis, Henoch-Schönlein purpura, hypertrophic osteoarthropathy, multicentric reticulohistiocytoma, surcoilosis, hemochromatosis, sickle cell anemia and other haemoglobinopathies, hyperlipoproteinemia, hypogammaglobulinemia, familial Mediterranean fever, Behat's disease, systemic lupus erythematosus, relapsing fever, psoriasis, multiple sclerosis, septicaemia, septic shock, multiple organ dysfunction syndrome, acute respiratory distress syndrome, chronic obstructive pulmonary disease, rheumatoid arthritis, acute lung injury, and broncho-pulmonary dysplasia, but the present invention is not limited thereto.

The term "infectious inflammatory disease" as used herein refers to, for example, one or more selected from the group consisting of salmonellosis, food poisoning, typhoid fever, paratyphoid fever, sepsis, septic shock, systemic inflammatory response syndrome (SIRS), multiple organ dysfunction syndrome (MODS), pneumonia, pulmonary tuberculosis, tuberculosis, colds, influenza, airway infections, rhinitis, nasopharyngitis, tympanitis, bronchitis, lymphadenitis, parotitis, lymphadenitis, cheilitis, stomatitis, arthritis, myositis, dermatitis, vasculitis, gingivitis, pericementitis, keratitis, conjunctivitis, wound infections, peritonitis, hepatitis, osteomyelitis, cellulitis, meningitis, encephalitis, brain abscesses, encephalomyelitis, meningitis, nephritis, carditis, endocarditis, enteritis, gastritis, esophagitis, duodenitis, colitis, urethritis, cystitis, vaginitis, cervicitis, salpingitis, infectious erythema, bacterial dysentery, ulcerative abscesses, bacteremia, diarrhea, dysentery, gastroenteritis, gastroenteritis, genitourinary abscesses, infections of open wounds or injuries, purulent inflammation, abscesses, boils, pyoderma, impetigo, folliculitis, cellulitis, wound infections after surgery, scaled-skin syndrome, skin burn syndrome, thrombotic thrombocytopenia, hemolytic uremic syndrome, renal failure, pyelonephritis, glomerulonephritis, nervous system abscesses, otitis media, sinusitis, pharyngitis, tonsillitis, mastoiditis, soft tissue inflammation, dental infections, dacryocystitis, pleurisy, abdominal abscesses, liver abscesses, cholecystitis, spleen abscesses, pericarditis, myocarditis, placentitis, amniotic fluid infections, mammitis, mastitis, puerperal fever, toxic shock syndrome, lyme disease, gas gangrene, atherosclerosis, *Mycobacterium avium* syndrome (MAC), enterohaemorrhagic *Escherichia coli* (EHEC) infections, enteropathogenic *Escherichia coli* (EPEC) infections, enteroinvasive *Escherichia coli* (EIEC) infections, methicillin-resistant *Staphylococcus aureus* (MRSA) infections, vancomycin-resistant *Staphylococcus aureus* (VRSA) infections, and listerosis.

As used herein, the term "digestive disease" may include, for example, gastritis, colitis, Crohn's disease, intestinal Behcet's disease, intestinal lesions, ulcerative colitis, hemorrhagic rectal ulcers, and pouchitis, but the present invention is not limited thereto.

As used herein, the term "metabolic disease" refers to a disease caused by abnormal carbohydrate or lipid metabolism, and in the present invention, the metabolic disease may include one or more disease selected from the group consisting of obesity, fatty liver, liver cirrhosis, liver ischemia, liver abscesses, hyperlipidemia, hypercholesterolemia, diabetes, dyslipidemia, atherosclerosis, coronary artery disease, alcoholic fatty hepatitis, non-alcoholic steatohepatitis, and stroke, but the present invention is not limited thereto.

As used herein, the term "cancer" refers to a disease caused by the proliferation of cancer cells by conversion of normal cells into cancer cells, and in the present invention, the cancer includes one or more disease selected from the group consisting of lung cancer, laryngeal cancer, oral cancer, esophagus cancer, gastric cancer, colon-rectal cancer, liver cancer, cholangiocarcinoma, pancreatic cancer, breast cancer, ovarian cancer, kidney cancer, bladder cancer, prostate cancer, cervical cancer, brain tumors, leukemia, and lymphoma, but the present invention is not limited thereto.

As used herein, the term "inflammatory skin disease" includes, but is not limited to, skin inflammation, psoriasis, lupus erythematous, dandruff, acute/chronic eczema, contact dermatitis, atopic dermatitis, seborrheic dermatitis, lichen simplex chronicus, intertrigo, exfoliative dermatitis, papular urticaria, solar dermatitis, and acne.

As used herein, the term "inflammatory cytokine" refers to, among trace amounts of bioactive substances produced by lymphocytes, macrophages, or the like, particularly cytokines that are deeply involved in inflammatory responses to bacterial or viral infections, tumors, tissue damage, and the like.

In the present invention, the inflammatory cytokine may be IL-1, IL-2, IL-3, IL-4, IL-5, IL-6, IL-7, IL-8, IL-9, IL-10, IL-11, IL-12, IL-13, TNF-α, TNF-β, transforming growth factor-β (TGF-β), MIG (CXCL9), or interferons (IFNs), but the present invention is not limited thereto.

As used herein, the term "interleukin-8 (IL-8)" refers to a basic protein having heparin affinity, which consists of a triple-stranded β-sheet structure and an a helix structure and has a molecular weight of about 8,000, which belongs to the chemokine family and is produced by various cells including macrophages during inflammation. The interleukin-8 chromosome gene consists of 4 active sites and 3 inactive sites, and the gene is activated by the synergistic action of NFkB, C/EBP, AP-1 binding elements present in the upstream region. Interleukin-8 is an essential factor involved in migration and activation of neutrophils in acute inflammatory responses.

The protein of the present invention may be isolated from a *Streptococcus pyogenes* culture broth.

The amount of the *Streptococcus pyogenes* culture broth or a protein isolated from the culture broth in the composition of the present invention may be appropriately adjusted depending on the symptoms of a disease, the degree of progression of symptoms, the condition of a patient, and the like, and may range from, for example, 0.0001 wt % to 99.9 wt % or 0.001 wt % to 50 wt % with respect to a total weight of the composition, but the present invention is not limited thereto. The amount ratio is a value based on the amount of dried product from which a solvent is removed.

The pharmaceutical composition according to the present invention may further include a suitable carrier, excipient, and diluent which are commonly used in the preparation of pharmaceutical compositions. The excipient may be, for example, one or more selected from the group consisting of a diluent, a binder, a disintegrant, a lubricant, an adsorbent, a humectant, a film-coating material, and a controlled release additive.

The pharmaceutical composition according to the present invention may be used by being formulated, according to commonly used methods, into a form such as powders, granules, sustained-release-type granules, enteric granules, liquids, eye drops, elixirs, emulsions, suspensions, spirits, troches, aromatic water, lemonades, tablets, sustained-release-type tablets, enteric tablets, sublingual tablets, hard capsules, soft capsules, sustained-release-type capsules, enteric capsules, pills, tinctures, soft extracts, dry extracts, fluid extracts, injections, capsules, perfusates, or a preparation for external use, such as plasters, lotions, pastes, sprays, inhalants, patches, sterile injectable solutions, or aerosols. The preparation for external use may have a formulation such as creams, gels, patches, sprays, ointments, plasters, lotions, liniments, pastes, or cataplasmas.

As the carrier, the excipient, and the diluent that may be included in the pharmaceutical composition according to the present invention, lactose, dextrose, sucrose, oligosaccharides, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil may be used.

For formulation, commonly used diluents or excipients such as fillers, thickeners, binders, wetting agents, disintegrants, and surfactants are used.

As additives of tablets, powders, granules, capsules, pills, and troches according to the present invention, excipients such as corn starch, potato starch, wheat starch, lactose, white sugar, glucose, fructose, D-mannitol, precipitated calcium carbonate, synthetic aluminum silicate, dibasic calcium phosphate, calcium sulfate, sodium chloride, sodium hydrogen carbonate, purified lanolin, microcrystalline cellulose, dextrin, sodium alginate, methyl cellulose, sodium carboxymethylcellulose, kaolin, urea, colloidal silica gel, hydroxypropyl starch, hydroxypropyl methylcellulose 1928, 2208, 2906, 2910, propylene glycol, casein, calcium lactate, and Primojel®; and binders such as gelatin, Arabic gum, ethanol, agar powder, cellulose acetate phthalate, carboxymethylcellulose, calcium carboxymethylcellulose, glucose, purified water, sodium caseinate, glycerin, stearic acid, sodium carboxymethylcellulose, sodium methylcellulose, methylcellulose, microcrystalline cellulose, dextrin, hydroxycellulose, hydroxypropyl starch, hydroxymethylcellulose, purified shellac, starch, hydroxypropyl cellulose, hydroxypropyl methylcellulose, polyvinyl alcohol, and polyvinylpyrrolidone may be used, and disintegrants such as hydroxypropyl methylcellulose, corn starch, agar powder, methylcellulose, bentonite, hydroxypropyl starch, sodium carboxymethylcellulose, sodium alginate, calcium carboxymethylcellulose, calcium citrate, sodium lauryl sulfate, silicic anhydride, 1-hydroxypropylcellulose, dextran, ion-exchange resin, polyvinyl acetate, formaldehyde-treated casein and gelatin, alginic acid, amylose, guar gum, sodium bicarbonate, polyvinylpyrrolidone, calcium phosphate, gelled starch, Arabic gum, amylopectin, pectin, sodium polyphosphate, ethyl cellulose, white sugar, magnesium aluminum silicate, a di-sorbitol solution, and light anhydrous silicic acid; and lubricants such as calcium stearate, magnesium stearate, stearic acid, hydrogenated vegetable oil, talc, lycopodium powder, kaolin, Vaseline, sodium stearate, cacao butter, sodium salicylate, magnesium salicylate, polyethylene glycol 4000, 6000, liquid paraffin, hydrogenated soybean oil (Lubri wax), aluminum stearate, zinc stearate, sodium lauryl sulfate, magnesium oxide, Macrogol, synthetic aluminum silicate, silicic anhydride, higher fatty acids, higher alcohols, silicone oil, paraffin oil, polyethylene glycol fatty acid ether, starch, sodium chloride, sodium acetate, sodium oleate, dl-leucine, and light anhydrous silicic acid may be used.

As additives of liquids according to the present invention, water, dilute hydrochloric acid, dilute sulfuric acid, sodium citrate, monostearic acid sucrose, polyoxyethylene sorbitol fatty acid esters (twin esters), polyoxyethylene monoalkyl ethers, lanolin ethers, lanolin esters, acetic acid, hydrochloric acid, ammonia water, ammonium carbonate, potassium hydroxide, sodium hydroxide, prolamine, polyvinylpyrrolidone, ethylcellulose, and sodium carboxymethylcellulose may be used.

In syrups according to the present invention, a white sugar solution, other sugars or sweeteners, and the like may be used, and as necessary, a fragrance, a colorant, a preservative, a stabilizer, a suspending agent, an emulsifier, a viscous agent, or the like may be used.

In emulsions according to the present invention, purified water may be used, and as necessary, an emulsifier, a preservative, a stabilizer, a fragrance, or the like may be used.

In suspensions according to the present invention, suspending agents such as acacia, tragacanth, methylcellulose, carboxymethylcellulose, sodium carboxymethylcellulose, microcrystalline cellulose, sodium alginate, hydroxypropyl methylcellulose 1828, 2906, 2910, and the like may be used, and as necessary, a surfactant, a preservative, a stabilizer, a colorant, and a fragrance may be used.

Injections according to the present invention may include: solvents such as distilled water for injection, a 0.9% sodium chloride solution, Ringer's solution, a dextrose solution, a dextrose+sodium chloride solution, PEG, lactated Ringer's solution, ethanol, propylene glycol, non-volatile oil-sesame oil, cottonseed oil, peanut oil, soybean oil, corn oil, ethyl oleate, isopropyl myristate, and benzene benzoate; cosolvents such as sodium benzoate, sodium salicylate, sodium acetate, urea, urethane, monoethylacetamide, butazolidine, propylene glycol, the Tween series, amide nicotinate, hexamine, and dimethylacetamide; buffers such as weak acids and salts thereof (acetic acid and sodium acetate), weak bases and salts thereof (ammonia and ammonium acetate), organic compounds, proteins, albumin, peptone, and gums; isotonic agents such as sodium chloride; stabilizers such as sodium bisulfite ($NaHSO_3$) carbon dioxide gas, sodium metabisulfite ($Na_2S_2O_3$), sodium sulfite ($Na_2SO_3$), nitrogen gas ($N_2$), and ethylenediamine tetraacetic acid; sulfating agents such as 0.1% sodium bisulfide, sodium formaldehyde sulfoxylate, thiourea, disodium ethylenediaminetetraacetate, and acetone sodium bisulfite; a pain relief agent such as benzyl alcohol, chlorobutanol, procaine hydrochloride, glucose, and calcium gluconate; and suspending agents such as sodium CMC, sodium alginate, Tween 80, and aluminum monostearate.

In suppositories according to the present invention, bases such as cacao butter, lanolin, Witepsol, polyethylene glycol, glycerogelatin, methylcellulose, carboxymethylcellulose, a mixture of stearic acid and oleic acid, Subanal, cottonseed oil, peanut oil, palm oil, cacao butter+cholesterol, lecithin, lanette wax, glycerol monostearate, Tween or span, imhausen, monolan (propylene glycol monostearate), glycerin, Adeps solidus, buytyrum Tego-G, cebes Pharma 16, hexalide base 95, cotomar, Hydrokote SP, S-70-XXA, S-70-XX75 (S-70-XX95), Hydrokote 25, Hydrokote 711, idropostal, massa estrarium (A, AS, B, C, D, E, I, T), masa-MF, masupol, masupol-15, neosuppostal-N, paramount-B, supposiro OSI, OSIX, A, B, C, D, H, L, suppository base IV types AB, B, A, BC, BBG, E, BGF, C, D, 299, suppostal N, Es, Wecoby W, R, S, M, Fs, and tegester triglyceride matter (TG-95, MA, 57) may be used.

Solid preparations for oral administration include tablets, pills, powders, granules, capsules, and the like, and such solid preparations are formulated by mixing the composition with at least one excipient, e.g., starch, calcium carbonate, sucrose, lactose, gelatin, and the like. In addition to simple excipients, lubricants such as magnesium stearate and talc are also used.

Examples of liquid preparations for oral administration include suspensions, liquids for internal use, emulsions, syrups, and the like, and these liquid preparations may include, in addition to simple commonly used diluents, such as water and liquid paraffin, various types of excipients, for example, a wetting agent, a sweetener, a fragrance, a preservative, and the like. Preparations for parenteral administration include an aqueous sterile solution, a non-aqueous solvent, a suspension, an emulsion, a freeze-dried preparation, and a suppository. Non-limiting examples of the non-aqueous solvent and the suspension include propylene glycol, polyethylene glycol, a vegetable oil such as olive oil, and an injectable ester such as ethyl oleate.

The pharmaceutical composition according to the present invention is administered in a pharmaceutically effective amount. In the present invention, the pharmaceutically effective amount refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields.

The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

The pharmaceutical composition of the present invention may be administered to an individual via various routes. All administration methods can be predicted, and the pharmaceutical composition may be administered via, for example, oral administration, subcutaneous injection, intraperitoneal administration, intravenous injection, intramuscular injection, intrathecal (space around the spinal cord) injection, sublingual administration, administration via the buccal mucosa, intrarectal insertion, intravaginal insertion, ocular administration, intra-aural administration, intranasal administration, inhalation, spraying via the mouth or nose, transdermal administration, percutaneous administration, or the like.

The pharmaceutical composition of the present invention is determined depending on the type of a drug, which is an active ingredient, along with various related factors such as a disease to be treated, administration route, the age, gender, and body weight of a patient, and the severity of diseases.

As used herein, the "subject" refers to a subject in need of treatment of a disease, and more specifically, refers to a mammal such as a human or a non-human primate, a mouse, a rat, a dog, a cat, a horse, and a cow, but the present invention is not limited thereto.

As used herein, the "administration" refers to providing a subject with a predetermined composition of the present invention by using an arbitrary appropriate method.

The term "prevention" as used herein means all actions that inhibit or delay the onset of a target disease. The term "treatment" as used herein means all actions that alleviate or beneficially change a target disease and abnormal metabolic symptoms caused thereby via administration of the pharmaceutical composition according to the present invention. The term "alleviation" as used herein means all actions that reduce the degree of parameters related to a target disease, e.g., symptoms via administration of the composition according to the present invention.

In another embodiment of the present invention, the present invention provides a food composition for preventing or alleviating one or more selected from the group consisting of an inflammatory disease, a metabolic disease, and cancer, comprising a *Streptococcus pyogenes* culture broth or a protein isolated from the culture broth as an active ingredient.

The food composition comprises a health functional food composition.

The health functional food composition according to the present invention may be used by adding an active ingredient as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the composition of the present invention is added in an amount of 15 wt % or less, preferably 10 wt % or less based on the raw materials. However, for long-term intake for the purpose of health and hygiene or for the purpose of health control, the amount may be less than the above-mentioned range.

Other ingredients are not particularly limited, except that the health functional food composition of the present invention contains the active ingredient as an essential ingredient at the indicated ratio, and the food composition of the present invention may contain various flavorants, natural carbohydrates, and the like, like a typical beverage, as an additional ingredient. Examples of the above-described natural carbohydrate include common sugars such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, and erythritol. As the flavorant other than those described above, a natural flavorant (thaumatin, stevia extract (for example, rebaudioside A, glycyrrhizin and the like), and a synthetic flavorant (saccharin, aspartame and the like) may be advantageously used. The proportion of the natural carbohydrate may be appropriately determined by the choice of those of ordinary skill in the art.

The health functional food composition of the present invention may contain various nutrients, vitamins, minerals (electrolytes), flavoring agents such as synthetic flavoring agents and natural flavoring agents, colorants and fillers (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in a carbonated beverage, or the like, in addition to the additives. These ingredients may be used either alone or in combinations thereof. The ratio of these additives may also be appropriately selected by those of ordinary skill in the art.

In another embodiment of the present invention, the present invention provides a cosmetic composition for preventing or alleviating an inflammatory skin disease, comprising a protein derived from a *Streptococcus pyogenes* as an active ingredient.

Examples of products to which the cosmetic composition of the present invention may be added include cosmetics such as astringents, skin softeners, nourishing toners, various creams, essences, packs, foundations, and the like, cleansings, face cleansers, soaps, treatments, beauty liquids, and the like. Particular preparations of the cosmetic composition of the present invention include a skin lotion, a skin softener, a skin toner, an astringent, a lotion, a milk lotion, a moisturizing lotion, a nourishing lotion, a massage cream, a nourishing cream, a moisturizing cream, a hand cream, an essence, a nourishing essence, a pack, a soap, a shampoo, a cleansing foam, a cleansing lotion, a cleansing cream, a body lotion, a body cleanser, an emulsion, a lipstick, a makeup base, a foundation, a press powder, a loose powder, an eye shadow, and the like.

A cosmetic composition of the present invention may further include a composition selected from the group consisting of water-soluble vitamins, oil-soluble vitamins, polymer peptides, polymeric polysaccharides, and sphingolipids.

The water-soluble vitamin may be any substance that is blendable with cosmetics, but examples thereof include vitamin B1, vitamin B2, vitamin B6, pyridoxine, pyridoxine hydrochloride, vitamin B12, pantothenic acid, nicotinic acid, nicotinic acid amide, folic acid, vitamin C, vitamin H, and the like, and salts thereof (thiamine hydrochloride, sodium ascorbate, and the like) or derivatives thereof (sodium ascorbic acid-2-phosphate, magnesium ascorbic acid-2-phosphate, and the like) are also included in water-soluble vitamins that may be used in the present invention. These water-soluble vitamins may be obtained by a conventional method such as microbial transformation, purification from a microbial culture, an enzyme method, or a chemical synthesis method.

The oil-soluble vitamins may be any substance that is blendable with cosmetics, but examples thereof include vitamin A, carotene, vitamin D2, vitamin D3, vitamin E (dl-α-tocopherol, d-α-tocopherol), or the like, and derivatives thereof (e.g., ascorbyl palmitate, ascorbyl stearate, ascorbyl dipalmitate, dl-α-tocopherol acetate, dl-α-tocopherol nicotinate, vitamin E, DL-pantothenyl alcohol, D-pantothenyl alcohol, pantothenyl ethylether) may also be included in the oil-soluble vitamins used in the present invention. These oil-soluble vitamins may be obtained by a conventional method such as microbial transformation, purification from a microbial culture, or enzymatic or chemical synthesis.

The polymer peptides may be any substance that is blendable with cosmetics, but examples thereof may include collagen, hydrolyzed collagen, gelatin, elastin, hydrolyzed elastin, and keratin. The polymer peptides may be purified and obtained by any conventional method such as purification from a microbial culture, an enzyme method, or a chemical synthesis method, or may generally be used by being purified from natural substances such as the dermis of a pig, a cow, or the like and silk fiber of silkworms.

The polymeric polysaccharides may be any substance that is blendable with cosmetics, and examples thereof may include hydroxyethyl cellulose, xanthan gum, sodium hyaluronate, and chondroitin sulfate or salts thereof (sodium salts). For example, chondroitin sulfate or salts thereof may generally be purified from mammals or fish and used.

The sphingolipids may be any substance that is blendable with cosmetics, and examples thereof may include ceramide, phytosphingosine, and sphingoglycolipid. The sphingolipids may be purified, by a conventional method, from mammals, fish, shellfish, yeast, or plants, or may be obtained by a chemical synthesis method.

The cosmetic composition of the present invention may include, as necessary, other ingredients mixed in conventional cosmetics along with the above essential ingredients.

Examples of additional ingredients to be mixed may include lipid components, a humectant, an emollient, a surfactant, organic and inorganic pigments, organic powder, a UV absorbent, a preservative, a sanitizer, an antioxidant, a plant extract, a pH adjuster, alcohol, pigments, flavors, a blood circulation promoter, a cooling agent, an anti-diaphoretic, and purified water.

The lipid components may include, for example, ester lipids, hydrocarbon lipids, silicone lipids, fluorine lipids, animal fats, vegetable oil, or the like.

The ester lipids may include, for example, glyceryl tri 2-ethylhexanoate, cetyl 2-ethylhexanoate, isopropyl myristate, butyl myristate, isopropyl palmitate, ethyl stearate, octyl palmitate, isocetyl isostearate, butyl stearate, ethyl linolate, isopropyl linolate, ethyl oleate, isocetyl myristate, isostearyl myristate, isostearyl palmitate, octyldodecyl myristate, isocetyl isostearate, diethyl sebacate, diisopropyl adipate, isoalkyl neopentanate, tri(capryl, capric acid)glyceryl, trimethylolpropane tri 2-ethylhexanoate, trimethylolpropane triisostearate, pentaerythritol tetra 2-ethylhexanoate, cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl palmitate, octyl stearate, isocetyl stearate, isodecyl oleate, octyldodecyl oleate, octyldodecyl linolate, isopropyl isostearate, cetostearyl 2-ethylhexanoate, stearyl 2-ethylhexanoate, hexyl isostearate, ethyleneglycol dioctanoate, ethyleneglycol dioleate, propyleneglycol dicaprinate, propyleneglycol di(caprylate, caprinate), propyleneglycol dicaprylate, neopentylglycol dicaprinate, neopentylglycol dioctanoate, glyceryl tricaprylate, glyceryl triundecylate, glyceryl triisopalmitate, glyceryl triisostearate, octyldodecyl neopentanoate, isostearyl octanoate, octyl isononanoate, hexyldecyl neodecanoate, octyldodecyl neodecanoate, isocetyl isostearate, isostearyl isostearate, octyldecyl isostearate, polyglycerin ester oleate, polyglycerin ester isostearate, triisocetyl citrate, triisoalkyl citrate, triisooctyl citrate, lauryl lactate, myristyl lactate, cetyl lactate, octyldecyl lactate, triethyl citrate, acetyltriethyl citrate, acetyltributyl citrate, trioctyl citrate, diisostearyl malate, 2-ethylhexyl hydroxystearate, di 2-ethylhexyl succinate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoyl hydroxystearate, stearoyl 12-stearoyl hydroxystearate, isostearyl 12-stearoyl hydroxystearate, and the like.

The hydrocarbon lipids may include, for example, squalene, liquid paraffin, alpha-olefin oligomers, isoparaffin, ceresine, paraffin, liquid isoparaffin, polybutene, microcrystalline wax, Vaseline, and the like.

The silicone lipids may include, for example, polymethyl silicon, methylphenyl silicon, methyl cyclopolysiloxane, octamethyl polysiloxane, decamethyl polysiloxane, dodecamethyl cyclosiloxane, dimethylsiloxane/methylcetyloxysiloxane copolymers, dimethylsiloxane/methylstearoxysiloxane copolymers, alkyl-modified silicon oil, amino-modified silicon oil, and the like.

The fluorine lipids may include perfluoropolyether and the like.

The animal or vegetable oil may include avocado oil, almond oil, olive oil, sesame oil, rice bran oil, safflower oil, soybean oil, corn oil, rape flower oil, apricot kernel oil, palm kernel oil, palm oil, castor oil, sunflower oil, grape seed oil, cotton seed oil, coconut oil, tallow nut oil, wheat germ oil, rice germ oil, Shea butter, evening primrose oil, macadamia nut oil, meadow foam seed oil, yolk oil, beef tallow, hemp seed oil, mink oil, orange roughy oil, jojoba oil, candelilla wax, carnauba wax, liquid lanolin, dehydrated castor oil, and the like.

The humectant may include water-soluble low molecular humectants, oil-soluble molecular humectants, water-soluble polymers, oil-soluble polymers, and the like.

The water-soluble low molecular humectants may include serine, glutamine, sorbitol, mannitol, pyrrolidone-sodium carboxylate, glycerin, propylene glycol, 1,3-butylene glycol, ethylene glycol, polyethylene glycol B (degree of polymerization: n=2 or higher), polypropylene glycol (degree of polymerization: n=2 or higher), polyglycerin B (degree of polymerization: n=2 or higher), lactic acid, lactates, and the like.

The oil-soluble low molecular humectants may include cholesterol, cholesterol ester, and the like.

The water-soluble polymers may include carboxyvinyl polymers, polyasparaginic acid salts, tragacanth, xanthan gum, methyl cellulose, hydroxymethyl cellulose, hydroxylethyl cellulose, hydroxypropyl cellulose, carboxymethyl cellulose, water-soluble chitin, chitosan, dextrin, and the like.

The oil-soluble polymers may include, for example, polyvinyl pyrrolidone/eicosen copolymers, polyvinyl pyrrolidone/hexadecene copolymers, nitrocellulose, dextrin fatty acid ester, silicone polymers, and the like.

The emollients may include, for example, long chain cholesterylester acyl glutamate, cholesteryl hydroxystearate, 12-hydroxystearic acid, stearic acid, rosin acid, lanolin fatty acid cholesteryl ester, and the like.

The surfactants may include, for example, non-ionic surfactants, anionic surfactants, cationic surfactants, amphoteric surfactants, and the like.

The non-ionic surfactants may include self-emulsion type glycerin monostearate, propyleneglycol fatty acid ester, glycerin fatty acid ester, polyglycerin fatty acid ester, sorbitan fatty acid ester, polyoxyethylene (POE) sorbitan fatty acid ester, POE sorbit fatty acid ester, POE glycerin fatty acid ester, POE alkylethers, POE fatty acid ester, POE dehydrated castor oil, POE castor oil, polyoxyethylene/polyoxypropylene (POE/POP) copolymers, POE/POP alkylethers, polyether-modified silicone, alkanolamide laurate, alkylamine oxide, hydrated soy phospholipids, and the like.

The anionic surfactants may include fatty acid soap, α-acylsulfonate, alkyl sulfonates, alkylallyl sulfonates, alkylnaphthalene sulfonates, alkyl sulfates, POE alkylether sulfates, alkylamide sulfates, alkyl phosphates, POE alkyl phosphates, alkylamide phosphates, alkyloyl alkyltaurin salts, N-acylamino acid salts, POE alkylether carboxylates, alkyl sulfosuccinates, sodium alkyl sulfoacetates, acylated hydrolyzed collagen peptide salts, perfluoroalkyl ester phosphates, and the like.

The cationic surfactants may include, for example, alkyltrimethylammonium chloride, stearyltrimethylammonium chloride, steraryltrimethylammonium bromide, cetostearyl trimethylammonium chloride, distearyl dimethylammonium chloride, stearylaryl dimethylbenzylammonium chloride, behenyltrimethylammonium bromide, benzalkonium chloride, diethylaminoethylamide stearate, dimethylaminopropylamide stearate, quaternary ammonium salts of lanolin derivatives, and the like.

The amphoteric surfactants may include carboxybetaine, amidebetaine, sulfobetaine, hydroxysulfobetaine, amidesulfobetaine, phosphobetaine, aminocarboxylate, imidazoline derivatives, amideamine-based amphoteric surfactants, and the like.

The organic and inorganic pigments may include: inorganic pigments such as silicic acid, anhydrous silicic acid, magnesium silicate, talc, sericite, mica, kaolin, bengala, clay, bentonite, titanium dioxide-coated mica, bismuth oxychloride, zirconium oxide, magnesium oxide, zinc oxide, titanium oxide, aluminum oxide, calcium sulfate, barium sulfate, magnesium sulfate, calcium carbonate, magnesium carbonate, iron oxide, ultramarine, chromium oxide, chromium hydroxide, calamine, and combinations thereof; organic pigments such as polyamide, polyester, polypropylene, polystyrene, polyurethane, vinyl resin, urea resin, phenol resin, fluorine resin, silicon resin, acryl resin, melamine resin, epoxy resin, polycarbonate resin, divinyl benzene/styrene copolymers, silk powder, cellulose, CI pigment yellow, and CI pigment orange; and composite pigments of inorganic and organic pigments.

The organic powder may include: metallic soap such as calcium stearate; metal salts of alkyl phosphoric acid such as zinc sodium cetylate, zinc laurylate, and calcium laurylate; polymetallic salts of acylamino acid such as calcium N-lauroyl-beta-alanine, zinc N-lauroyl-beta-alanine, and calcium N-lauroylglycine; polymetallic salts of amide sulfonates such as calcium N-lauroyl-taurine and calcium N-palmitoyl-taurine; N-acyl alkaline amino acids such as N-epsilon-lauroyl-L-lysine, N-epsilon-palmitoyl lysine, N-α-palmitoylol nitin, N-α-lauroyl arginine, and N-α-dehydrated tallow fatty acid acyl arginine; N-acyl polypeptides such as N-lauroyl glycylglycine; α-amino fatty acids such as α-aminocaprylic acid and α-aminolauric acid; polyethylene; polypropylene; nylon; polymethylmethacrylate; polystyrene; divinylbenzene/styrene copolymers; ethylene tetrafluoride; and the like.

The UV absorbents may include para-aminobenzoic acid, ethyl para-aminobenzoate, amyl para-aminobenzoate, octyl para-aminobenzoate, ethyleneglycol salicylate, phenyl salicylate, octyl salcylate, benzyl salicylate, butylphenyl salicylate, homomentyl salicylate, benzyl cinnamate, paramethoxycinnamic acid-2-ethoxylethyl, octyl paramethoxycinnamate, mono-2-ethylhexaneglyceryl diparamethoxycinnamate, isopropyl paramethoxycinnamate, diisopropyl/diisopropyl cinnamic acid ester mixtures, urocanic acid, ethyl urocanate, hydroxymethoxybenzophenone, hydroxymethoxybenzophenone sulfonic acid and salts thereof, dihydroxymethoxybenzophenone, sodium dihydroxymethoxybenzophenone disulfonate, dihydroxybenzophenone, tetrahydroxybenzophenone, 4-tert-butyl-4'-methoxydibenzoylmethane, 2,4,6-trianilino-p-(carbo-2'-ethylhexyl-1'-oxy)-1,3,5-triazine, 2-(2-hydroxy-5-methylphenyl)benzotriazole, and the like.

The sanitizers may include hinokitiol, trichloric acid, trichlorohydroxydiphenylether, chlorohexidine gluconate, phenoxyethanol, resorcine, isopropylmethylphenol, azulene, salicylic acid, zinc pyrithione, benzalkonium chloride, light sensitive element No. 301, sodium mononitroguaiacol, undecylenic acid, and the like.

The antioxidants may include butylhydroxyanisole, propyl gallate, elisorbic acid, and the like.

The pH adjusters may include citric acid, sodium citrate, malic acid, sodium malate, fumaric acid, sodium fumarate, succinic acid, sodium succinate, sodium hydroxide, sodium monohydrophosphate, and the like.

The alcohols may include higher alcohols such as cetyl alcohol.

In addition, additional ingredients to be mixed are not limited to the above examples, and any one of the above ingredients may be mixed within a range that does not adversely affect the objectives and effects of the present invention, but may range from 0.01 wt % to 5 wt % or 0.01 wt % to 3 wt % with respect to the total weight of the composition.

For lotion, paste, cream, or gel preparations of the present invention, as a carrier ingredient, animal fiber, vegetable fiber, wax, paraffin, starch, tragacanth, a cellulose derivative, polyethylene glycol, silicon, bentonite, silica, talc, zinc oxide, or the like may be used.

For powder or spray preparations of the present invention, lactose, talc, silica, aluminum hydroxide, calcium silicate, or polyamide powder may be used as a carrier ingredient. In particular, in the case of spray preparations, the composition may further include a propellant such as chlorofluorohydrocarbon, propane/butane, or dimethyl ether.

For solution or emulsion preparations of the present invention, a solvent, a solubilizing agent, or an emulsifying agent may be used as a carrier ingredient, and the carrier ingredient may be, for example, water, ethanol, isopropanol, ethyl carbonate, ethyl acetate, benzyl alcohol, benzyl benzoate, propylene glycol, 1,3-butyl glycol oil, a glycerol aliphatic ester, polyethylene glycol, or a sorbitan fatty acid ester.

For suspension preparations of the present invention, as a carrier ingredient, a liquid diluent such as water, ethanol, or propylene glycol, a suspending agent such as ethoxylated isostearyl alcohol, polyoxyethylene sorbitol ester, or polyoxyethylene sorbitan ester, micro-crystalline cellulose, aluminum methahydroxide, bentonite, agar, tragacanth, or the like may be used.

For surfactant-containing cleansing preparations of the present invention, as a carrier ingredient, an aliphatic alcohol sulfate, an aliphatic alcohol ether sulfate, a sulfosuccinate monoester, isethionate, imidazolinium derivatives, methyltaurate, sarcosinate, fatty acid amide ether sulfate, alkylamidobetaine, an aliphatic alcohol, a fatty acid glyceride, a fatty acid diethanol amide, vegetable oil, a lanolin derivative, an ethoxylated glycerol fatty acid ester, or the like may be used.

In another embodiment of the present invention, the present invention provides an inhalant composition for preventing or alleviating a respiratory inflammatory disease, comprising a *Streptococcus pyogenes* culture broth or a protein isolated from the culture broth as an active ingredient.

An inhalant composition of the present invention may comprise not only a *Streptococcus pyogenes* culture broth or a protein isolated from the culture broth, but also ingredients commonly used in inhalant compositions, and may comprise, for example, general adjuvants such as an antioxidant, a stabilizer, a solubilizing agent, vitamins, pigments, and flavors, and a carrier.

According to an exemplary embodiment of the present invention, the amount of the *Streptococcus pyogenes* culture broth or the protein isolated from the culture broth of the present invention may range from 0.00001 wt % to 99 wt %, preferably 0.0001 wt % to 50 wt %, preferably 0.5 wt % to 20 wt %, and more preferably 1.0 wt % to 10 wt %, with respect to the total weight of the composition, but the present invention is not limited thereto.

Modes of the Invention

Hereinafter, preferred Examples for helping the understanding of the present invention will be suggested. However, the following Examples are provided only to more easily understand the present invention, and the contents of the present invention are not limited by the following Examples.

Example 1

Example 1. Effect of *Streptococcus Pyogenes*-Derived Cell Culture Broth on Inhibiting Expression of Inflammatory Cytokine IL-8 in Gastric Epithelial Cell Line (AGS)

A *Streptococcus pyogenes* strain was thawed in a 37° C. bath as quickly as possible, 100 μl of the strain was spread on an MRS agar medium, and incubated in a 10% $CO_2$ incubator at 37° C. for 24 hours, and then a single colony of *Streptococcus pyogenes* was collected and shake-cultured in 1 L of a brain heart infusion (BHI) broth in a 10% $CO_2$ incubator at 37° C. and 200 rpm for 24 hours.

After shake culturing, the resultant broth was transferred to a 500 ml high-speed centrifugation tube and subjected to high-speed centrifugation at 10,000×g for 30 minutes to collect the supernatant (SP CM) excluding *Streptococcus pyogenes* cells, and in order to produce SP CM not containing extracellular vesicles (EVs), the SP CM produced according to the above method was subjected to ultracentrifugation at 100,000×g for 2 hours to collect the supernatant (SP CM EV(−)) excluding a precipitate.

$1\times10^8$ gastric epithelial cells (AGS) were released in a nucleated cell culture medium (RPMI, 10% FBS, antibiotics), dispensed into a 100 mm cell culture dish, and incubated in a 5% $CO_2$ incubator at 37° C. for 24 hours, and then the nucleated cell culture medium was removed, and the cells were treated with 1 ml of trypsin-EDTA (0.05%) and left at 37° C. for 5 minutes. After 5 minutes, floating cells were collected with 5 ml of a cell culture medium, dispensed into a 15 ml tube, and centrifuged at 1,500 rpm for 5 minutes, and then the existing cell culture medium was removed, and the cells were diluted in a new cell culture medium to a concentration of $1\times10^5$/ml of gastric epithelial cells (AGS) and 1 ml of the resultant medium was dispensed into each well of a 12-well plate, followed by incubation in a 5% $CO_2$ incubator at 37° C. for 24 hours.

After incubation, the cell culture medium was replaced with a new cell culture medium, and a negative control (NT) was treated with PBS, a positive control (PT) was treated with IL-1α (10 ng/ml), and experimental groups (Exp1 and Exp2) were treated with SP CM (10 μl) and SP CM EV(−) (10 μl) along with IL-1α, and each group was incubated in a 5% $CO_2$ incubator at 37° C. for 24 hours, and then each cell culture broth was obtained to quantify the extent of expression of the inflammatory cytokine IL-8 by ELISA (using a standard protocol).

As a result of treating the gastric epithelial cell line (AGS) with IL-1α or SP CM and SP CM EV(-) along with IL-1α according to the above method and then analyzing the extent of IL-8 expression by ELISA, as illustrated in FIG. 1, it was confirmed that both SP CM and SP CM EV(-) inhibited the expression of inflammatory cytokine IL-8, induced by IL-1α, which indicates that the active ingredient that inhibits IL-8 expression is a water-soluble ingredient (see FIG. 1).

Example 2. Effect of *Streptococcus Pyogenes*-Derived Cell Culture Broth Concentrated with 100 kDa Ultrafiltration Filter on Inhibiting Expression of Inflammatory Cytokine IL-8 in Gastric Epithelial Cell Line (AGS)

To characterize the active ingredient for inhibiting IL-8 expression of a *Streptococcus pyogenes*-derived cell culture broth, a *Streptococcus* culture broth was separated using the following method.

A *Streptococcus pyogenes* strain was thawed in a 37° C. bath as quickly as possible, 100 µl of the strain was spread on an MRS agar medium, and incubated in a 10% $CO_2$ incubator at 37° C. for 24 hours, and then a single colony of *Streptococcus pyogenes* was collected and shake-cultured in 1 L of a brain heart infusion (BHI) broth in a 10% $CO_2$ incubator at 37° C. and 200 rpm for 24 hours, followed by transfer to a 500 ml high-speed centrifugation tube and subjected to high-speed centrifugation at 10,000×g for 30 minutes to collect the supernatant (SP CM) excluding *Streptococcus pyogenes* cells.

1 L of the produced SP CM was subjected to ultrafiltration (using a standard protocol) using a Quixstand benchtop system (GE Healthcare) and a 100 kDa ultrafiltration filter (GE Healthcare), and the buffer was replaced with 2 L of phosphate buffered saline (PBS) to produce 100 ml of SP CM that was unable to pass through a 100 kDa ultrafiltration filter. Subsequently, the SP CM produced using the method of Example 1 was ultracentrifuged to thereby finally produce SP CM>100 kDa from which a water-insoluble component was removed and only a water-soluble portion was contained.

$1 \times 10^8$ gastric epithelial cells (AGS) were released in a nucleated cell culture medium (RPMI, 10% FBS, antibiotics), dispensed into a 100 mm cell culture dish, and incubated in a 5% $CO_2$ incubator at 37° C. for 24 hours, and then the nucleated cell culture medium was removed, and the cells were treated with 1 ml of trypsin-EDTA (0.05%) and left at 37° C. for 5 minutes. After 5 minutes, floating cells were collected with 5 ml of a cell culture medium, dispensed into a 15 ml tube, and centrifuged at 1,500 rpm for 5 minutes, and then the existing cell culture medium was removed, and the cells were diluted in a new cell culture medium to a concentration of $1 \times 10^5$/ml of gastric epithelial cells (AGS) and 1 ml of the resultant medium was dispensed into each well of a 12-well plate, followed by incubation in a 5% $CO_2$ incubator at 37° C. for 24 hours.

After incubation, the cell culture medium was replaced with a new cell culture medium, and a negative control (NT) was treated with PBS, a positive control (PT) was treated with IL-1α (10 ng/ml), and an experimental group (Exp) was treated with the acquired pyogenes CM>100 kDa (10 µl) along with IL-1α, and each group was incubated in a 5% $CO_2$ incubator at 37° C. for 24 hours, and then each cell culture broth was obtained to quantify the extent of expression of the inflammatory cytokine IL-8 by ELISA (using a standard protocol).

Figure 2:
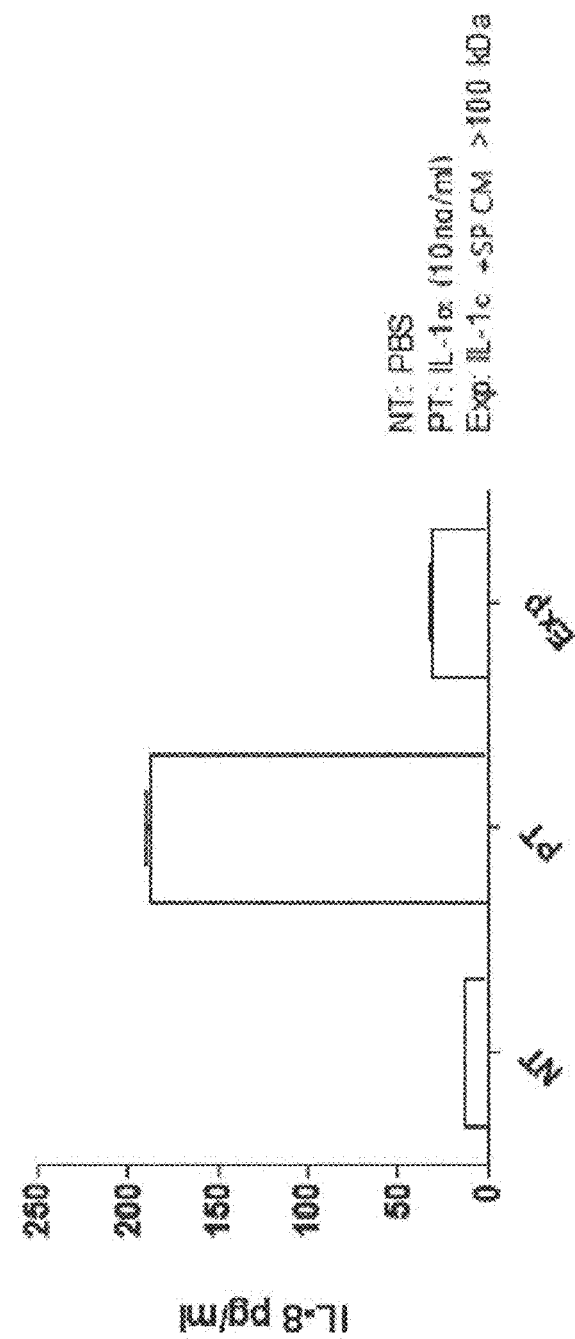
FIG. 2 illustrates the results of evaluating the IL-8 expression inhibitory activity of water-soluble components of a *Streptococcus pyogenes* culture broth (SP CM>100 kDa) obtained by removing low-molecular-weight compounds and proteins having a molecular weight smaller than 100 kDa through a 100 kDa filter, and ultracentrifuging the resulting solution to remove a non-water-soluble portion.

As a result of treating the gastric epithelial cell line (AGS) with IL-1α or SP CM>100 kDa along with IL-1α according to the above method and then analyzing the extent of IL-8 expression by ELISA, as illustrated in FIG. 2, it was confirmed that the water-soluble component in SP CM>100 kDa inhibited the expression of inflammatory cytokine IL-8, induced by IL-1α (see FIG. 2).

Example 3. IL-8 Expression Inhibitory Effect of Heat-Treated *Streptococcus Pyogenes*-Derived Cell Culture Broth To characterize the active ingredient for inhibiting IL-8 expression of a *Streptococcus pyogenes*-derived cell culture broth, a heat-treated *Streptococcus* culture broth was separated using the following method.

A *Streptococcus pyogenes* strain was thawed in a 37° C. bath as quickly as possible, 100 µl of the strain was spread on an MRS agar medium, and incubated in a 10% $CO_2$ incubator at 37° C. for 24 hours, and then a single colony of *Streptococcus pyogenes* was collected and shake-cultured in 1 L of a brain heart infusion (BHI) broth in a 10% $CO_2$ incubator at 37° C. and 200 rpm for 24 hours, followed by transfer to a 500 ml high-speed centrifugation tube and subjected to high-speed centrifugation at 10,000×g for 30 minutes to collect the supernatant (SP CM) excluding *Streptococcus pyogenes* cells.

1 L of the produced *pyogenes* CM 1 was subjected to ultrafiltration (using a standard protocol) using a Quixstand benchtop system (GE Healthcare) and a 100 kDa ultrafiltration filter (GE Healthcare), and the buffer was replaced with 2 L of phosphate buffered saline (PBS) to finally produce 100 ml of SP CM that was unable to pass through the 100 kDa ultrafiltration filter.

Subsequently, the SP CM produced using the method of Example 1 was ultracentrifuged to thereby finally produce SP CM>100 kDa from which a water-insoluble component was removed and only a water-soluble portion was contained, and in order to analyze the chemical properties of the produced SP CM>100 kDa, the SP CM>100 kDa was left at 100° C. for 15 minutes and then left again at 4° C. for 10 minutes.

$1 \times 10^8$ gastric epithelial cells (AGS) were released in a nucleated cell culture medium (RPMI, 10% FBS, antibiotics), dispensed into a 100 mm cell culture dish, and incubated in a 5% $CO_2$ incubator at 37° C. for 24 hours, and then the nucleated cell culture medium was removed, and the cells were treated with 1 ml of trypsin-EDTA (0.05%) and left at 37° C. for 5 minutes. After 5 minutes, floating cells were collected with 5 ml of a cell culture medium, dispensed into a 15 ml tube, and centrifuged at 1,500 rpm for 5 minutes, and then the existing cell culture medium was removed, and the cells were diluted in a new cell culture medium to a concentration of $1 \times 10^5$/ml of gastric epithelial cells (AGS) and 1 ml of the resultant medium was dispensed into each well of a 12-well plate, followed by incubation in a 5% $CO_2$ incubator at 37° C. for 24 hours.

After incubation, the cell culture medium was replaced with a new cell culture medium, and a negative control (NT) was treated with PBS, a positive control (PT) was treated with IL-1α (10 ng/ml), and experimental groups (Exp1 and Exp2) were treated with the acquired SP CM>100 kDa (10 µl) or heat-treated (H.I.) SP CM>100 kDa (10 µl) along with IL-1α, and each group was incubated in a 5% $CO_2$ incubator at 37° C. for 24 hours, and then each cell culture broth was obtained to quantify the extent of expression of the inflammatory cytokine IL-8 by ELISA (using a standard protocol).

Figure 3:
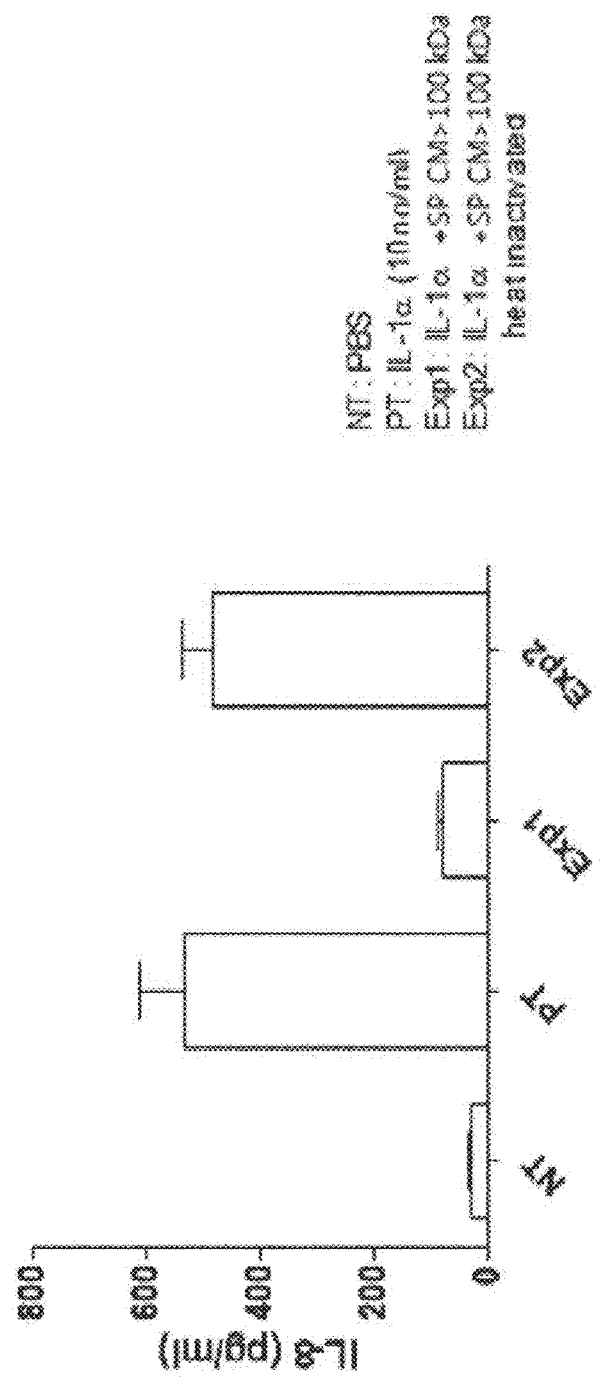
FIG. 3 illustrates the results of evaluating the IL-8 expression inhibitory activity of a *Streptococcus pyogenes* culture broth (SP CM>100 kDa) that was heat-treated.

As a result of treating the gastric epithelial cell line (AGS) with IL-1α and SP CM>100 kDa or SP CM>100 kDa H.I. along with IL-1α according to the above method and then analyzing the extent of IL-8 expression by ELISA, as illustrated in FIG. 3, it was confirmed that, while SP CM>100 kDa inhibited IL-8, SP CM>100 kDa H.I. was unable to inhibit the expression of IL-8. This indicates that the active ingredient of SP CM>100 kDa, inhibiting the expression of IL-8, is a protein component that is susceptible to heat (see FIG. 3).

Effect of SP CM>100 kDa on Inhibiting Expression of Inflammatory Cytokine IL-8 by *Helicobacter Pylori* (HP99) in Gastric Epithelial Cell Line (AGS)

SP CM>100 kDa, which is a water-soluble component, was separated and purified from a *Streptococcus pyogenes*-derived cell culture broth using the method of Example 2, and in order to evaluate whether SP CM>100 kDa is able to inhibit IL-8 expression caused by *Helicobacter pylori* (HP99) in a gastric epithelial cell line (AGS), *Helicobacter pylori* (HP99) was cultured using the following method.

A *Helicobacter pylori* HP99 stock was quickly thawed in 37° C. water, and 100 µl of the thawed stock was dispensed into a sheep blood agar plate and incubated in a 10% $CO_2$ incubator at 37° C. for 72 hours. After incubation, the *Helicobacter pylori* on the plate was scrapped off with a sterile cotton swab and released in a brain heart infusion broth, followed by dilution to an absorbance (O.D.) of 2.32.

To evaluate whether SP CM>100 kDa inhibits IL-8 expression caused by *Helicobacter pylori* (HP99) in a gastric epithelial cell line (AGS), the gastric epithelial cell line (AGS) was cultured using the method of Example 1.

After culture, the cell culture medium was replaced with a new cell culture medium, a negative control (NT) was treated with PBS, a positive control (PT) was treated with *Helicobacter pylori* (HP99, 10 µl), and an experimental group (Exp) was treated with the acquired SP CM>100 kDa (10 µl) along with *Helicobacter pylori*, and each group was incubated in a 5% $CO_2$ incubator at 37° C. for 24 hours, and then each cell culture broth was obtained to quantify the extent of expression of the inflammatory cytokine IL-8 by ELISA (using a standard protocol).

Figure 4:
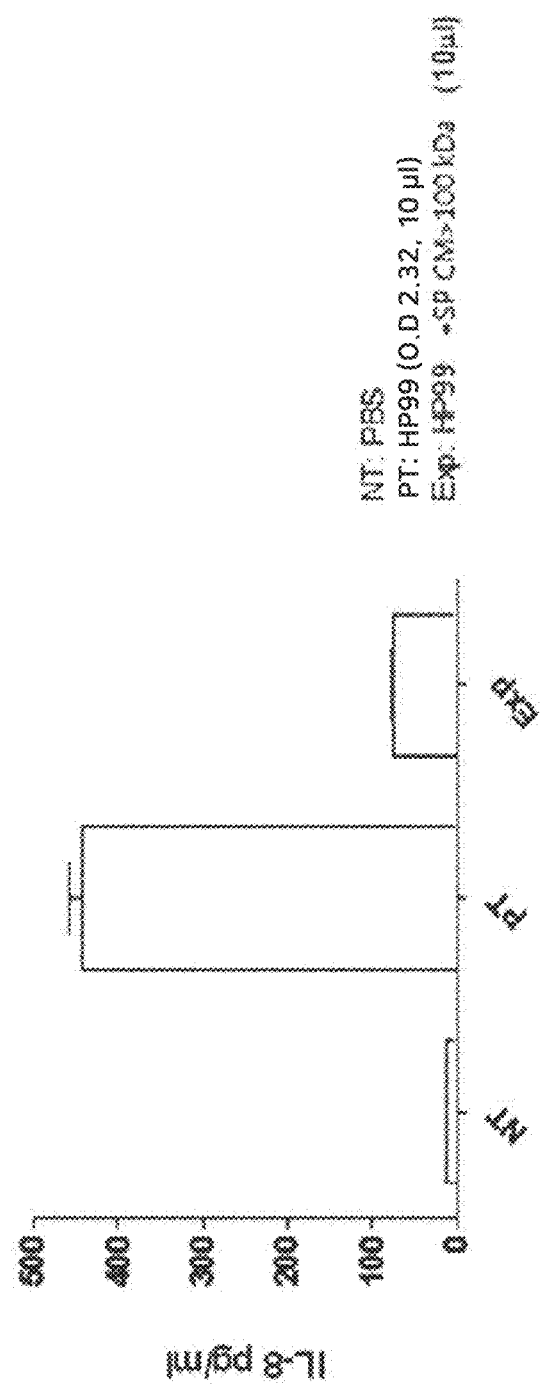
FIG. 4 illustrates the results of evaluating the efficacy of a *Streptococcus pyogenes* culture broth (SP CM>100 kDa) on inhibiting the expression of IL-8, which is induced by *Helicobacter pylori* (HP99), in a gastric epithelial cell strain (AGS).

As a result of treating the gastric epithelial cell line (AGS) with *Helicobacter pylori* (HP99) or pyogenes CM>100 kDa along with *Helicobacter pylori* according to the above method and then analyzing the extent of IL-8 expression by ELISA, as illustrated in FIG. 4, it was confirmed that the water-soluble component of SP CM>100 kDa inhibited IL-8 expression by *Helicobacter pylori* in the cell line AGS (see FIG. 4).

Example 5. Effect of SP CM>100 kDa on Inhibiting Expression of Inflammatory Cytokine IL-8 in Colon Epithelial Cell Line The effect of SP CM>100 kDa on inhibiting IL-8 expression induced by *E. coli*-derived extracellular vesicles (*E. coli* C4 EVs) in a colon epithelial cell line (HT29) was evaluated as follows.

$1 \times 10^8$ colon epithelial cells (HT29) were released in a nucleated cell culture medium (RPMI, 10% FBS, antibiotics), dispensed into a 100 mm cell culture dish, and incubated in a 5% $CO_2$ incubator at 37° C. for 24 hours, and then the nucleated cell culture medium was removed, and the cells were treated with 1 ml of trypsin-EDTA (0.05%) and left at 37° C. for 5 minutes. After 5 minutes, floating cells were collected with 5 ml of a cell culture medium, dispensed into a 15 ml tube, and centrifuged at 1,500 rpm for 5 minutes, and then the existing cell culture medium was removed, and the cells were diluted in a new cell culture medium to a concentration of $1 \times 10^5$/ml of HP29 cells and 1 ml of the resultant medium was dispensed into each well of a 12-well plate, followed by incubation in a 5% $CO_2$ incubator at 37° C. for 24 hours.

After incubation, the cell culture medium was replaced with a new cell culture medium, a negative control (NT) was treated with PBS, a positive control (PT) was treated with *E. coli* C4 EV (1 µg/ml), an experimental group (Exp) was treated with the acquired SP CM>100 kDa (10 µl) along with *E. coli* C4 EVs, each group was incubated in a 5% $CO_2$ incubator at 37° C. for 24 hours, and then each cell culture broth was obtained to quantify the extent of expression of the inflammatory cytokine IL-8 by ELISA (using a standard protocol).

Figure 5:
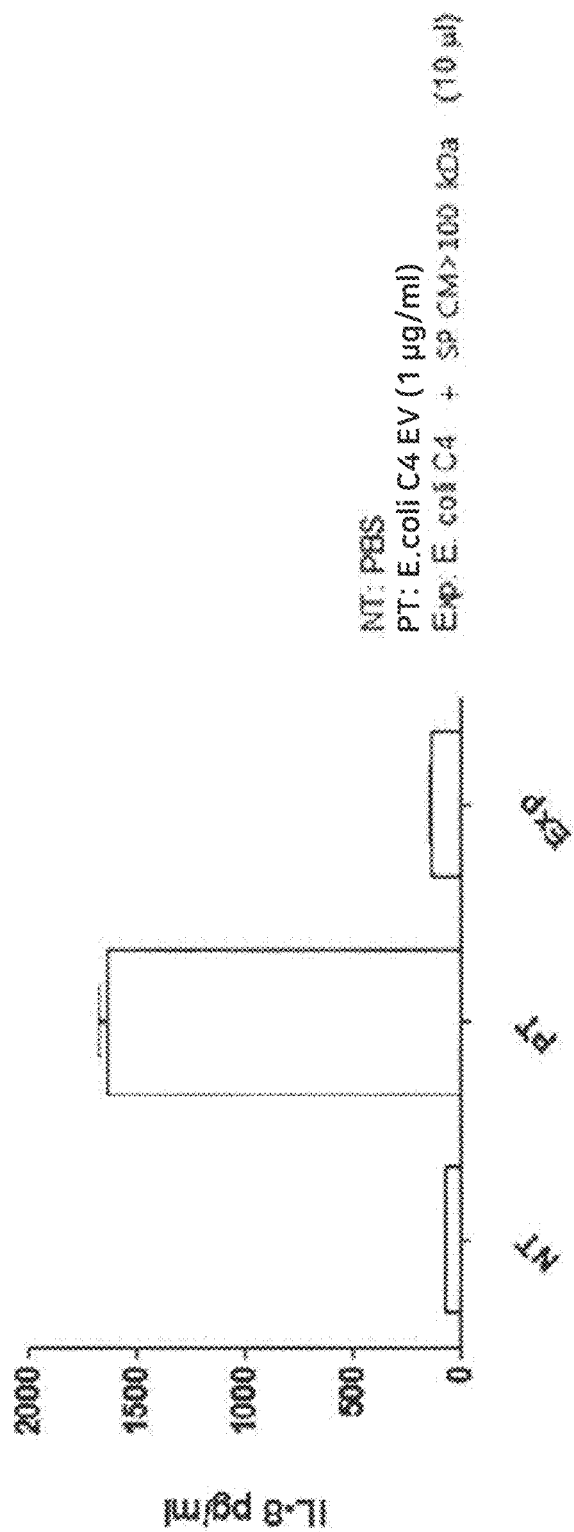
FIG. 5 illustrates the results of evaluating the efficacy of a *Streptococcus pyogenes* culture broth (SP CM>100 kDa) on inhibiting the expression of IL-8, which is induced by *E. coli*-derived extracellular vesicles, in a colon epithelial cell line (ATCC HTB-38).

As a result of treating the colon epithelial cell line (HT29) with *E. coli*-derived extracellular vesicles (*E. coli* C4 EVs), or SP CM>100 kDa along with *E. coli*-derived extracellular vesicles (*E. coli* C4 EVs) according to the above method and then analyzing the extent of IL-8 expression by ELISA, as illustrated in FIG. 5, it was confirmed that the water-soluble component of SP CM>100 kDa inhibited IL-8 expression induced by *E. coli*-derived extracellular vesicles (*E. coli* C4 EVs) (see FIG. 5).

Example 6. Isolation of Component from SP CM>100 kDa and Effectiveness Evaluation of Isolated Component To analyze the composition of water-soluble components of SP CM>100 kDa, 50 µl of SP CM>100 kDa was mixed with 6× native loading dye, and as a result of performing native PAGE (using a standard protocol) using a 6% native polyacryl amide gel, about five protein bands were identified.

Figure 6A:
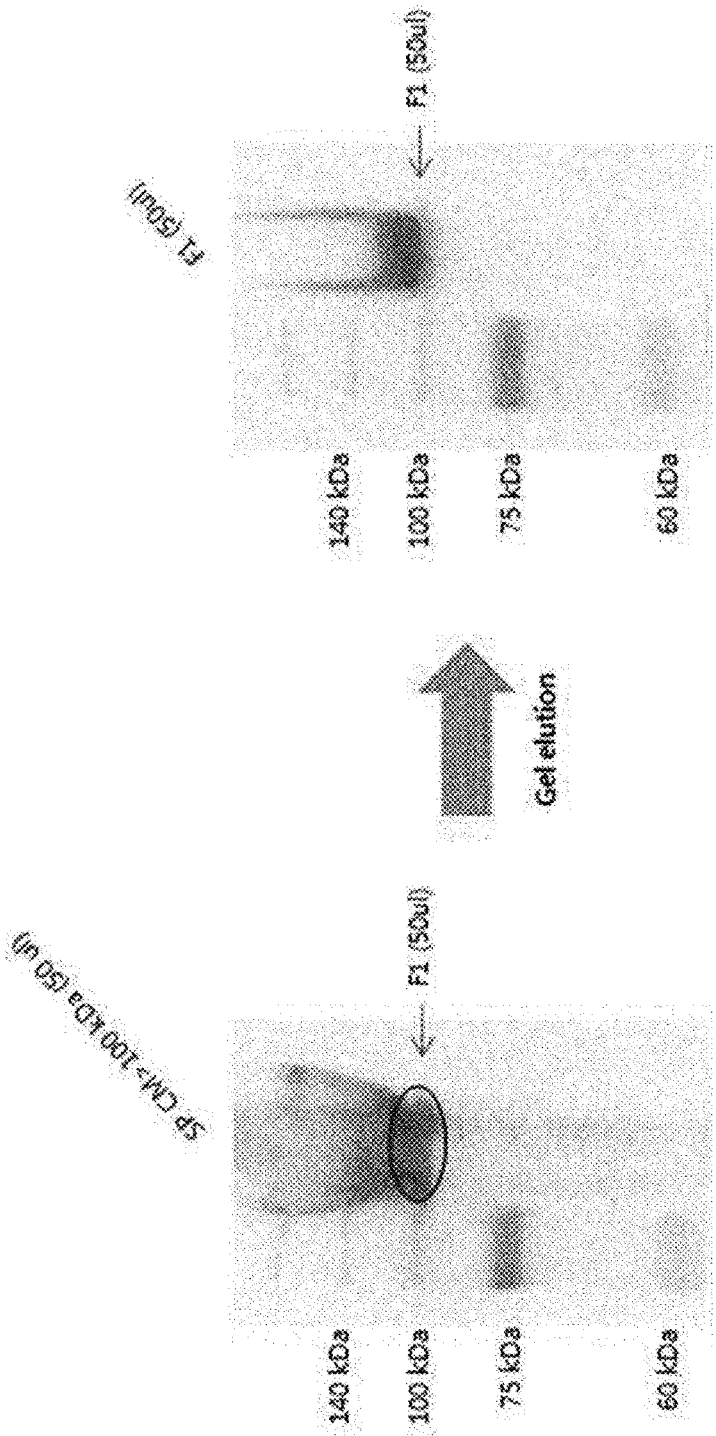
FIG. 6A illustrates the results of analyzing the composition of proteins of a *Streptococcus pyogenes* culture broth (SP CM>100 kDa) by 1D native-polyacrylamide gel electrophoresis (PAGE) and separating and purifying a high concentration of a protein (F1) from among the proteins.

For component separation, a protein expressed at the highest level and having a size of 100 kDa was purified, and for purification, an excess amount (500 µg) of SP CM>100 kDa was loaded onto a 6% native polyacryl amide gel to perform native PAGE, and the gel of the corresponding size was excised with a knife, placed in a gel elusion buffer (using a standard protocol), crushed with a homogeneous pestle, shaken at 200 rpm and 25° C., and left for 24 hours. Thereafter, gel by-products were filtered via a 100 µm mesh to obtain only a liquid, and only 50 µl thereof was subjected to native PAGE to confirm whether the 100 kDa protein (F1) was satisfactorily separated (see FIG. 6A).

To evaluate the effectiveness of the 100 kDa protein (F1) separated from SP CM>100 kDa, as described in Example 1, the expression of the inflammatory cytokine IL-8 in gastric epithelial cells (AGS) was examined.

Figure 6B:
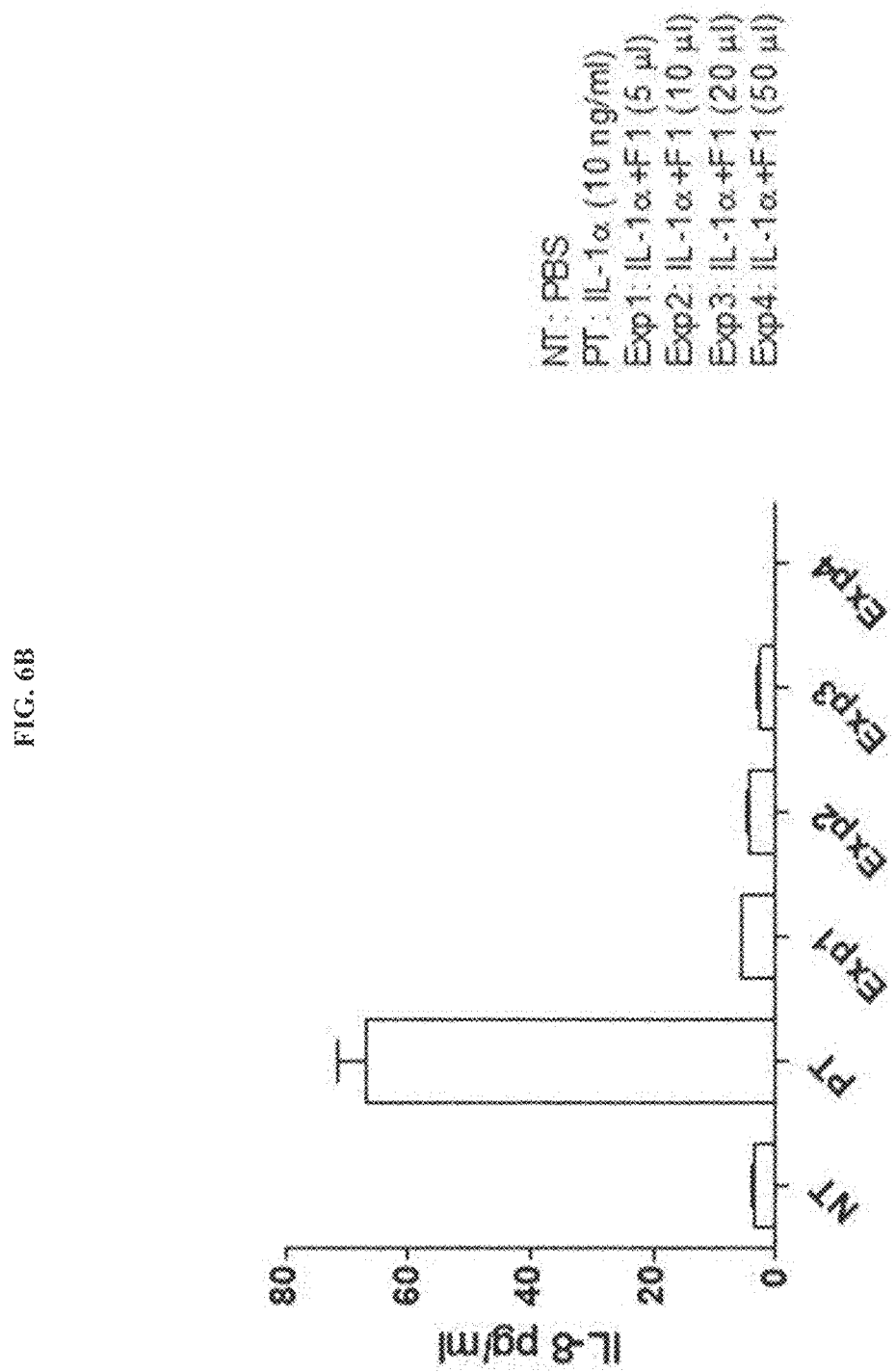
FIG. 6B illustrates the results of evaluating the IL-8 expression inhibitory activity of F1 that was separated and purified from a *Streptococcus pyogenes* culture broth (SP CM>100 kDa).

As a result of treating the gastric epithelial cell line (AGS) with IL-1α, or the separated 100 kDa protein (F1) at various volumes (5 µl, 10 µl, 20 µl, or 50 µl) along with IL-1α according to the above method and, after 24 hours, analyzing the extent of IL-8 expression by ELISA, as illustrated in FIG. 6B, it was confirmed that the 100 kDa protein (F1) inhibited IL-8 expression induced by IL-1α in the cell line AGS in a concentration-dependent manner (see FIG. 6B).

Figure 7:
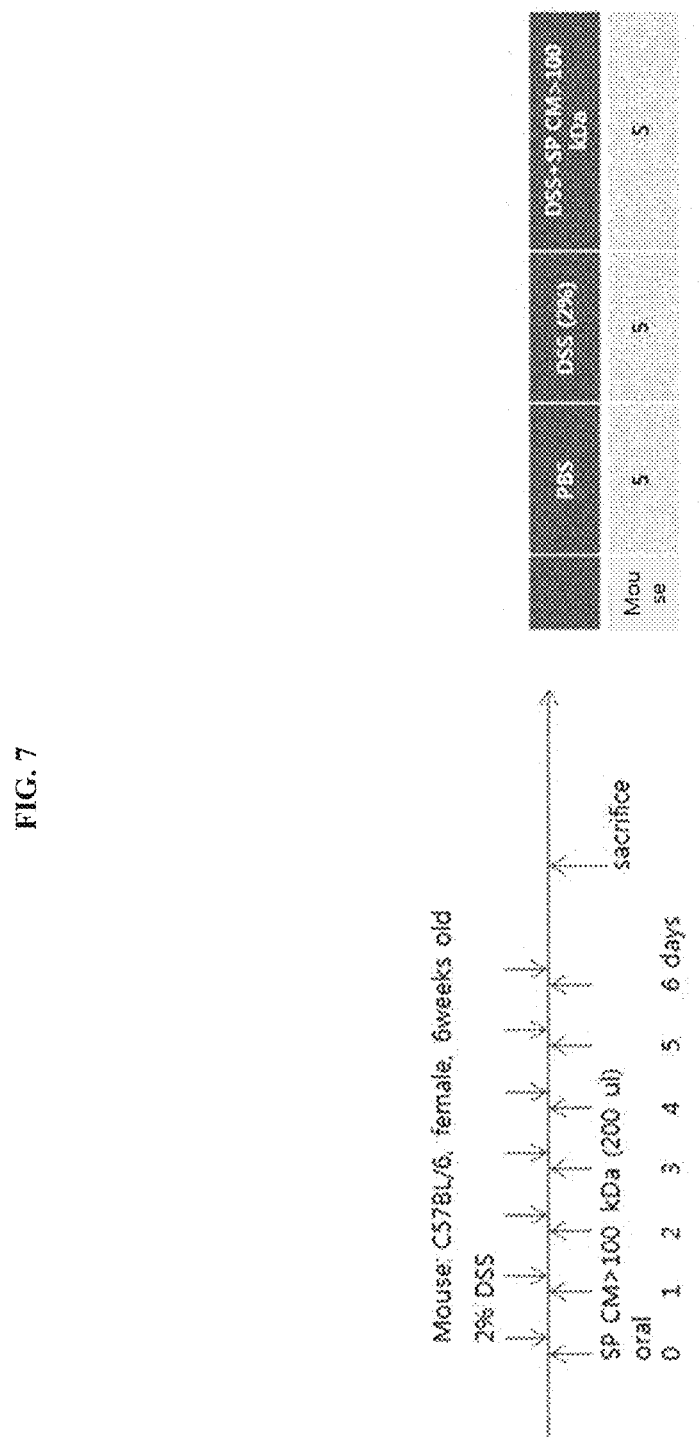
FIG. 7 depicts a protocol for evaluating the efficacy of a *Streptococcus pyogenes* culture broth (SP CM>100 kDa) in a dextran sulfate sodium (DSS)-induced colitis (DSS-colitis) mouse model.

Example 7. Anti-inflammatory Effect of SP CM>100 kDa in Dextran Sulfate Sodium (DSS)-Induced Colitis Mouse Model To evaluate the efficacy of SP CM>100 kDa in a dextran sulfate sodium (DSS)-induced colitis mouse model, an experiment was carried out using the method illustrated in FIG. 7 as follows.

15 female C57BL/6 mice at an age of 6 weeks were grouped into 5 mice per cage and placed in cages without discrimination, and after an acclimatization period of 2 days, the mice were fed drinking water (sterile water) diluted with 2% DSS from 9 a.m. to 6 p.m. from day 2 and fed general drinking water from 6 p.m. to 9 a.m. on the next day for 7 days. A group for evaluating the efficacy of SP CM>100 kDa was orally administered 200 μl of the SP CM>100 kDa produced using the method of Example 2 for 7 days by using a sonde (rod for oral administration) at 9 a.m. During the experimental period, the body weight, feed intake, degree of stool hardness, and extent of hematochezia of mice were measured, and after 7 days, the mice were dissected to evaluate the length of the large intestine of each mouse.

Figure 8A:
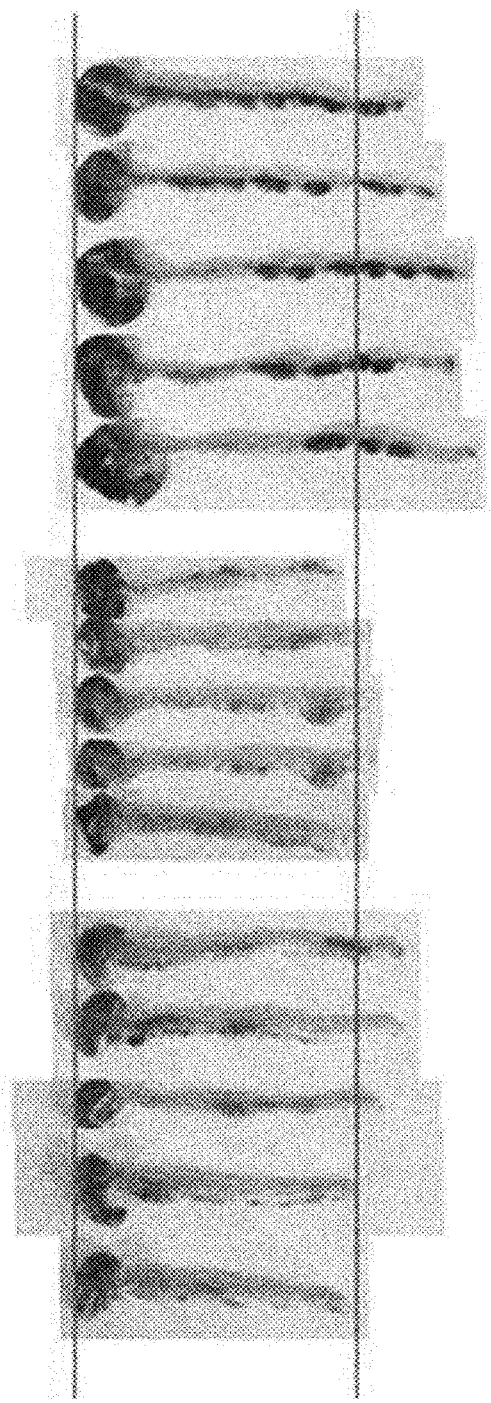
FIG. 8A illustrates the results of evaluating the efficacy of a *Streptococcus pyogenes* culture broth (SP CM>100 kDa) by measuring the lengths of large intestines of mice, in a dextran sulfate sodium (DSS)-induced colitis (DSS-colitis) mouse model.
Figure 8B:
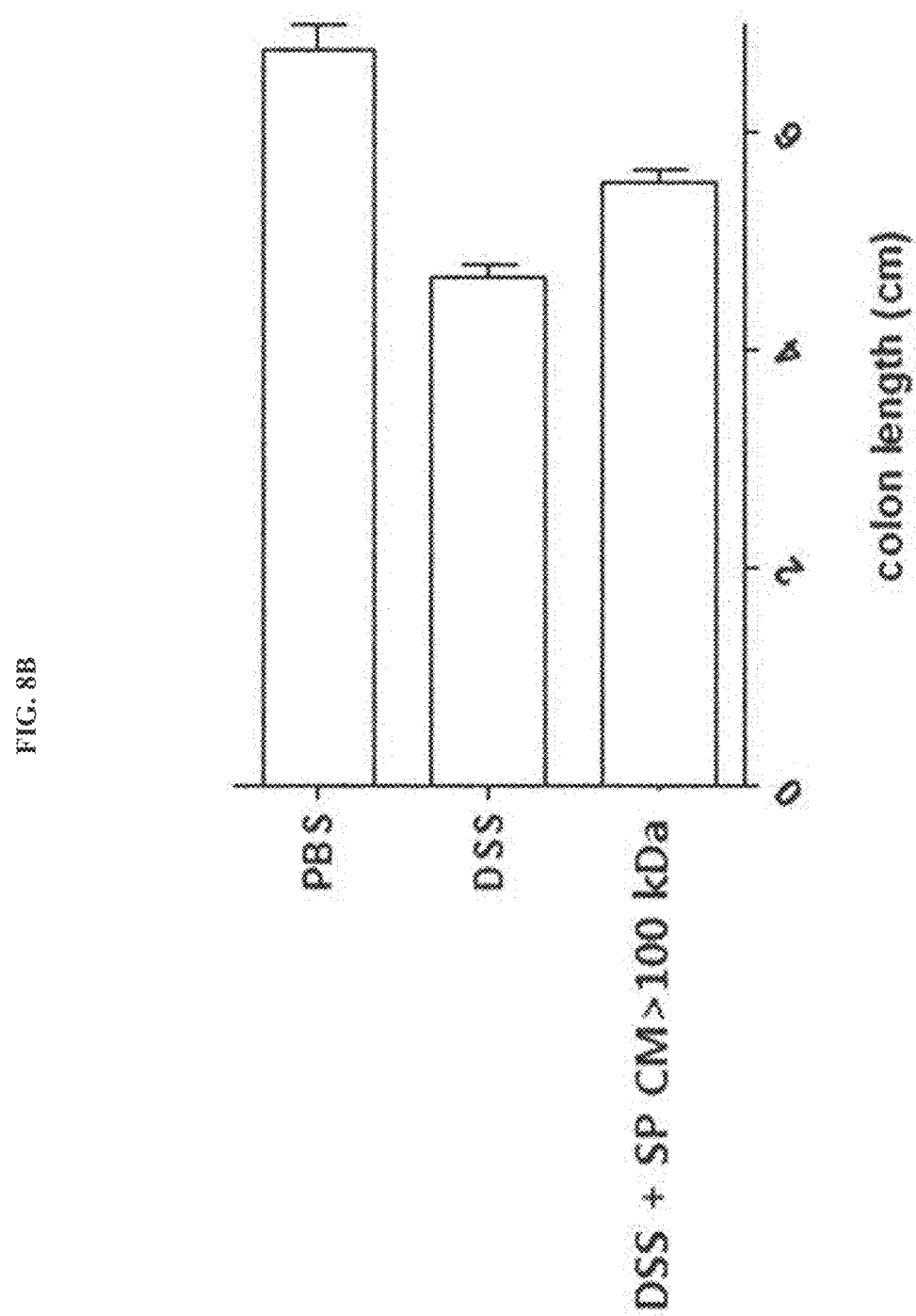
FIG. 8B is a graph showing the results of FIG. 8A.
Figure 9A:
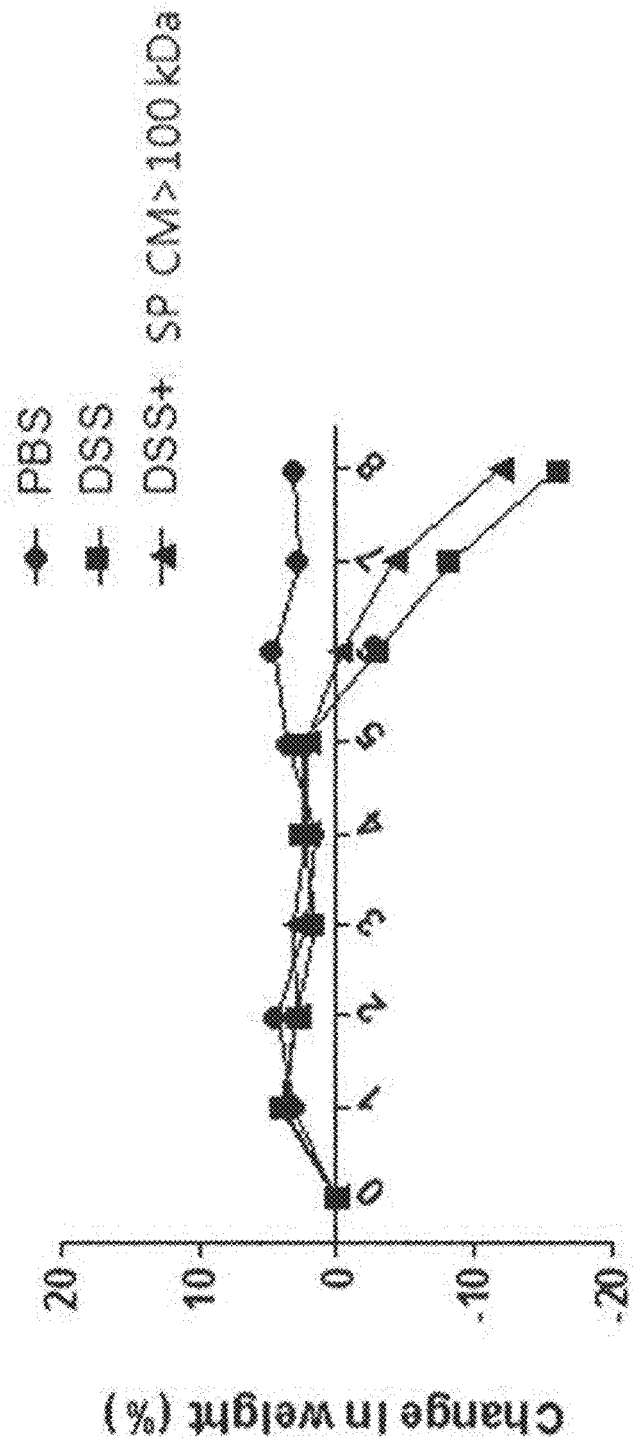
FIG. 9A illustrates the results of evaluating the efficacy of a *Streptococcus pyogenes* culture broth (SP CM>100 kDa) by measuring a change in weight of mice, in a dextran sulfate sodium (DSS)-induced colitis (DSS-colitis) mouse model.
Figure 9B:
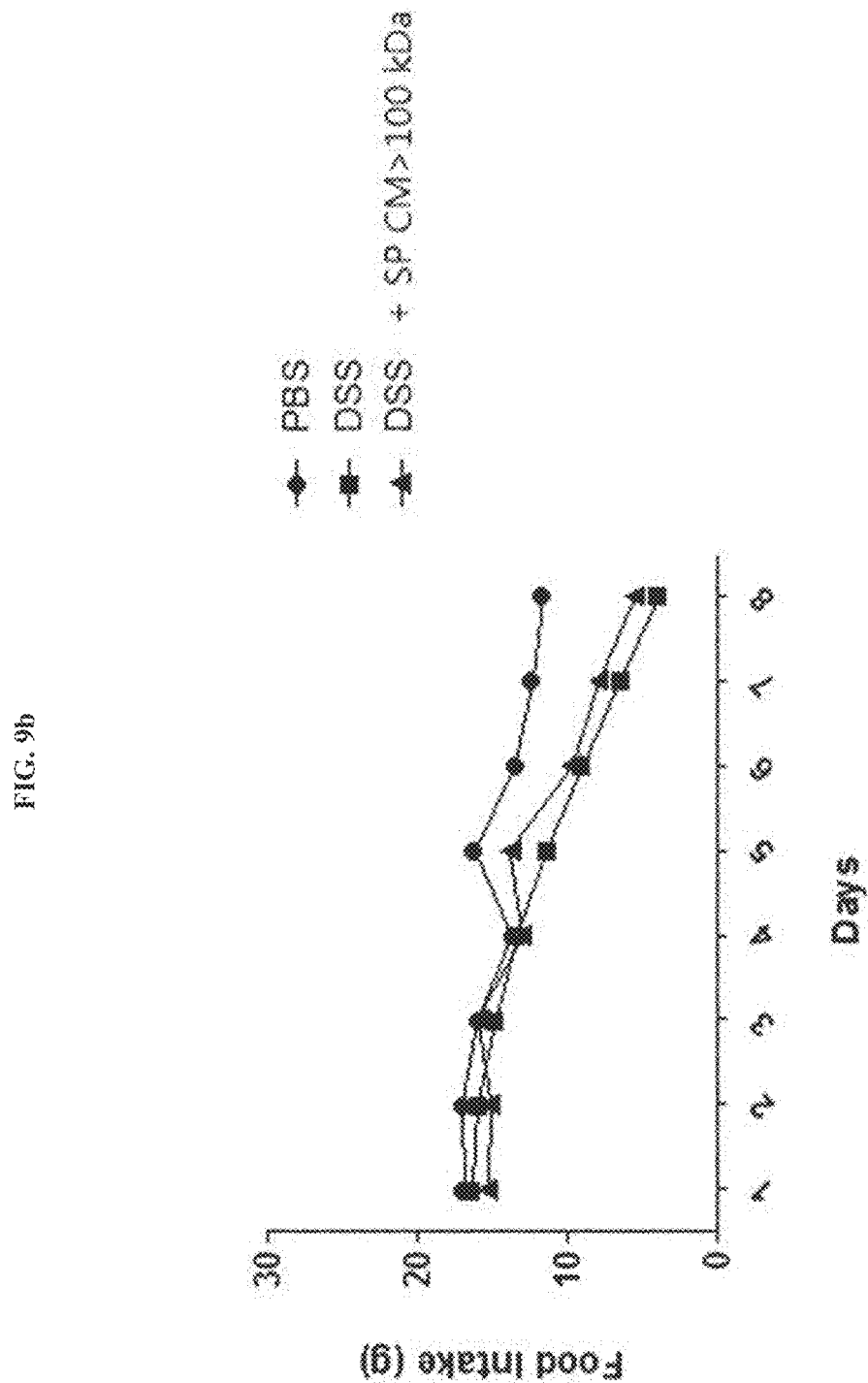
FIG. 9B illustrates the results of evaluating the efficacy of a *Streptococcus pyogenes* culture broth (SP CM>100 kDa) by measuring the food intake of mice, in a dextran sulfate sodium (DSS)-induced colitis (DSS-colitis) mouse model.

As a result of orally administering the DSS-induced colitis mouse model SP CM>100 kDa for 7 days according to the above method and observing the length of large intestine (see FIGS. 8A and 8B), changes in body weight (see FIG. 9A), feed intake (see FIG. 9B), and disease scores (see FIG. 10A), a greater length of large intestine, a smaller change in body weight, a greater feed intake, and a lower disease score were exhibited in the case of administering SP CM>100 kDa to the DSS-induced colitis mouse model, compared with the DSS-induced colitis mouse model.

The above results mean that SP CM>100 kDa has an anti-inflammatory effect in a mouse model with colitis induced by DSS.

Figure 11:
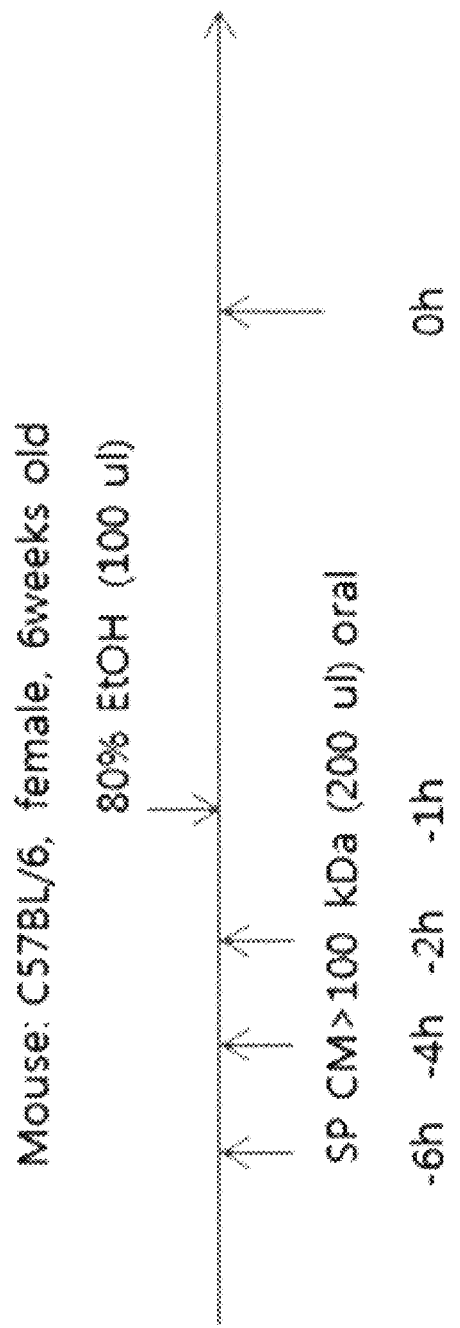
FIG. 11 depicts a protocol for evaluating the efficacy of a *Streptococcus pyogenes* culture broth (SP CM>100 kDa) in an ethanol-induced acute gastritis mouse model.

Example 8. Anti-inflammatory Effect of SP CM>100 kDa in Ethanol (EtOH)-Induced Acute Gastritis Mouse Model To evaluate the efficacy of SP CM>100 kDa in an ethanol-induced gastritis mouse model, an experiment was carried out using the method illustrated in FIG. 11 as follows.

6-week-old female C57BL/6 mice were grouped into 5 mice per cage and placed in cages without discrimination, and after an acclimatization period of 2 days, the mice were fasted for 24 hours after day 2, and a group for evaluating the efficacy of SP CM>100 kDa was orally administered 200 μl of the SP CM>100 kDa produced using the method of Example 2 by using a sonde (rod for oral administration) three times at 2-hour intervals from 9 a.m. 1 hour after the final administration of SP CM>100 kDa, 100 μl of 80% ethanol was orally administered to each mouse, and at 1 hour after administration, the mice were dissected to measure the shape, size, and extent of inflammation of the stomach.

Figure 12A:
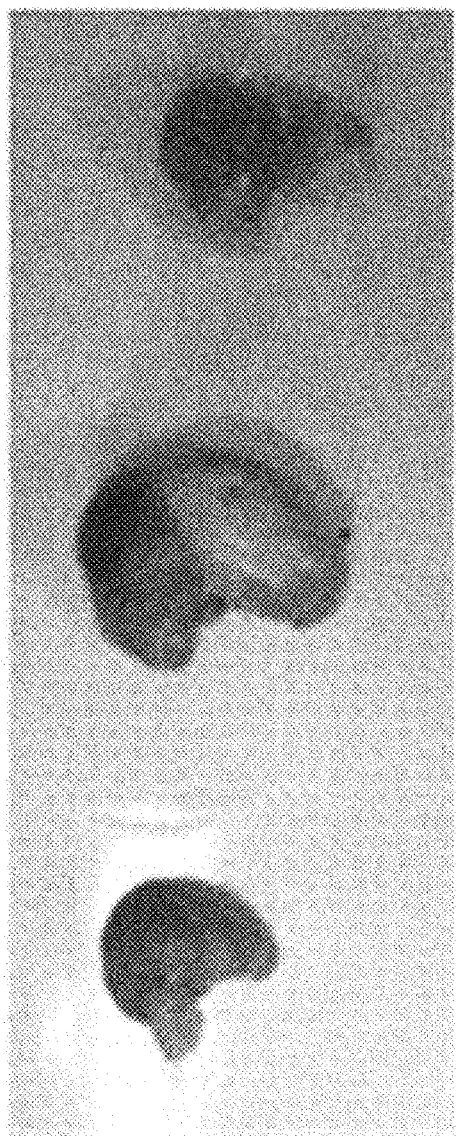
FIG. 12A illustrates the results of evaluating the anti-inflammatory efficacy of a *Streptococcus pyogenes* culture broth (SP CM>100 kDa) by observing changes in appearance and size of the stomach of mice in an ethanol-induced acute gastritis mouse model.
Figure 12B:
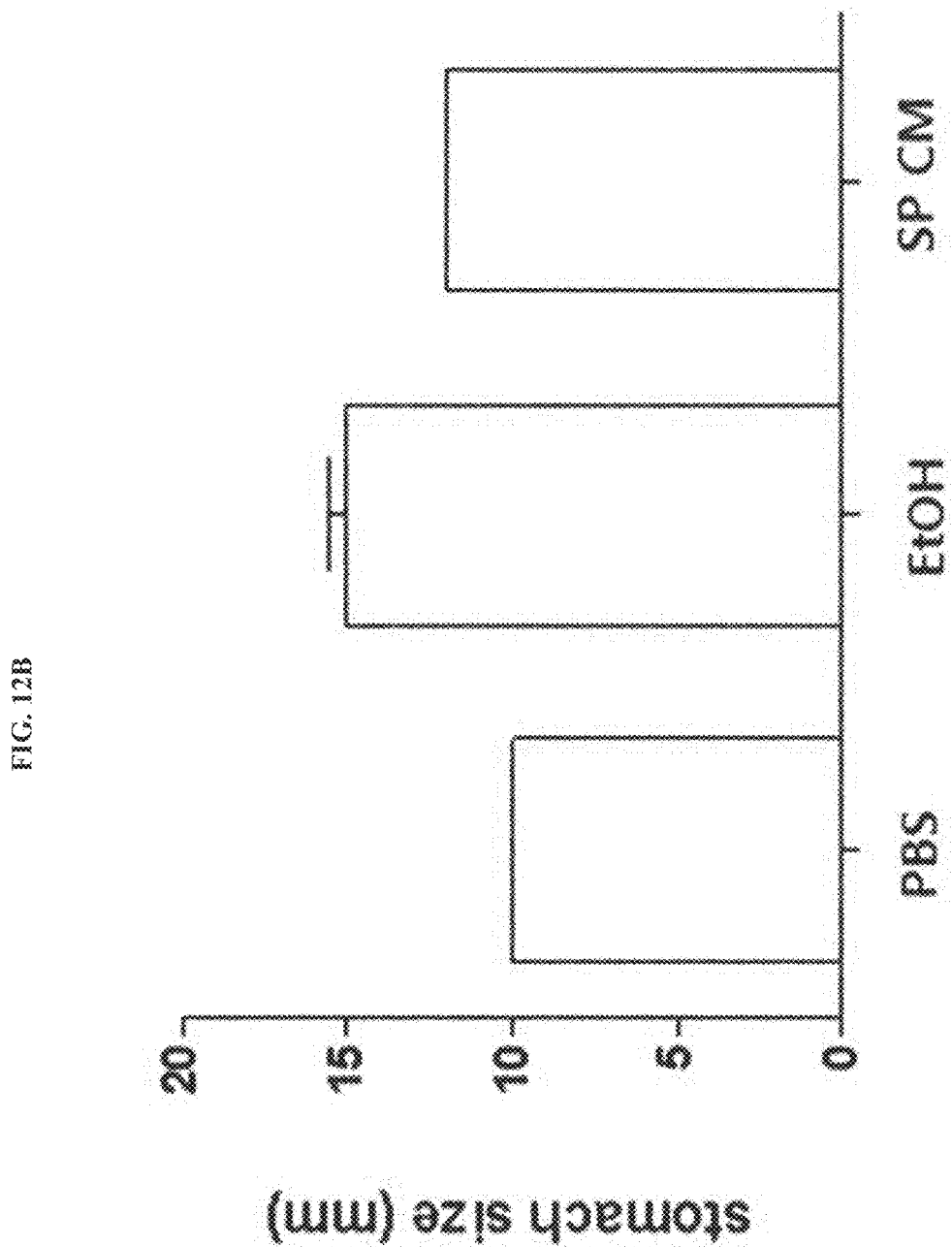
FIG. 12B is a graph showing the results of the change in stomach size of FIG. 12A.
Figure 12C:
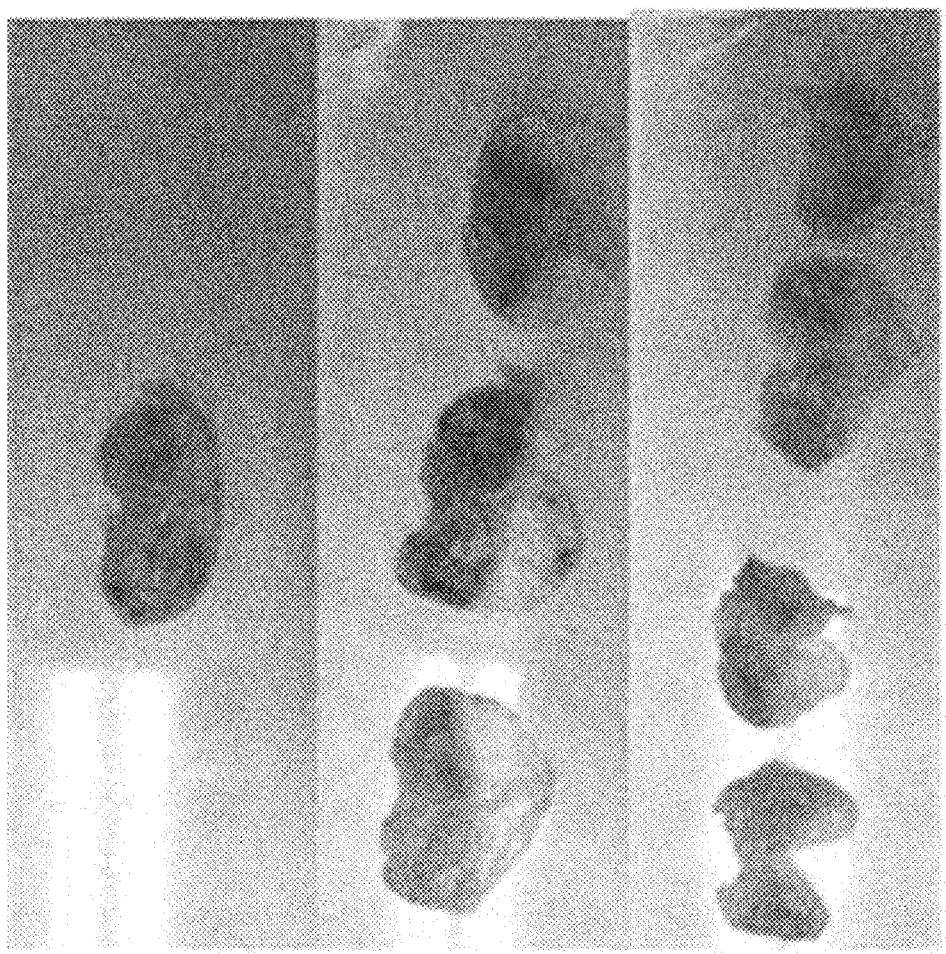
FIG. 12C illustrates the results of evaluating the anti-inflammatory efficacy of a *Streptococcus pyogenes* culture broth (SP CM>100 kDa) by observing the extent of gastric inflammation in an ethanol-induced acute gastritis mouse model.
Figure 12D:
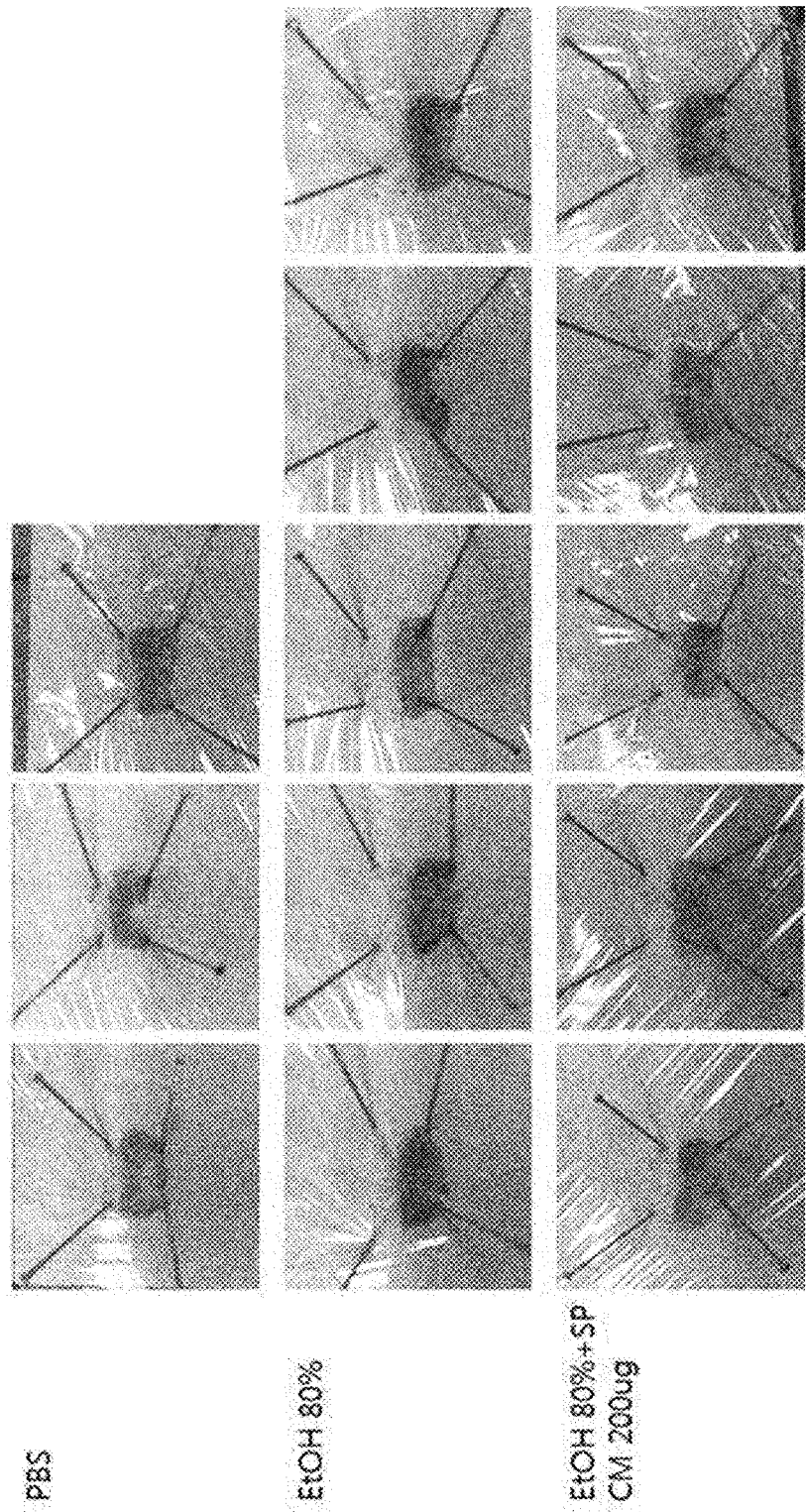
FIG. 12D illustrates the results of evaluating the anti-inflammatory efficacy of a *Streptococcus pyogenes* culture broth (SP CM 200 μg) by observing the degree of salt crystals in the stomach in an 80% ethanol-induced acute gastritis mouse model.

As a result of administering SP CM>100 kDa three times according to the above method and observing the shape (see FIG. 12A), size (see FIG. 12B), and extent of inflammation (see FIGS. 12C and 12D) of the stomach in the ethanol-induced gastritis mouse model, a smaller stomach size and a smaller extent of inflammation of the stomach were exhibited in the case of administering SP CM>100 kDa to the ethanol-induced gastritis mouse model, compared with the ethanol-induced gastritis mouse model.

The above results mean that SP CM>100 kDa has an anti-inflammatory effect in the ethanol-induced gastritis mouse model.

Example 9. Anticancer Effect of SP CM>100 kDa in Mouse Cancer Model

Figure 13:
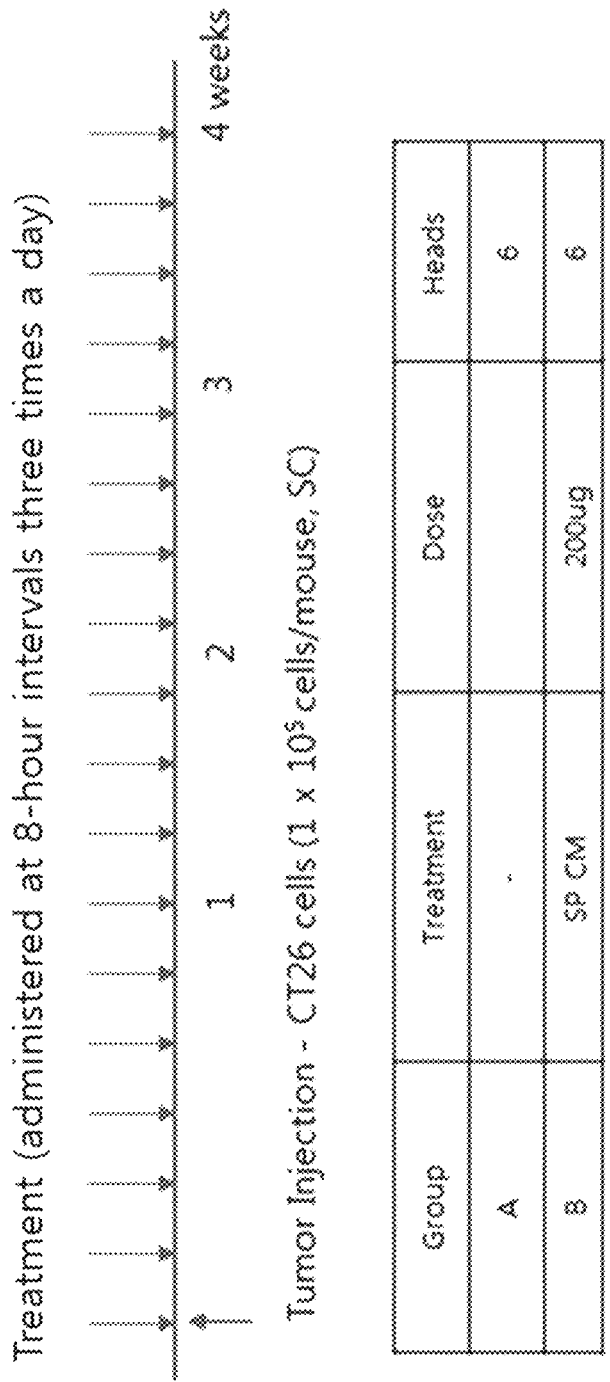
FIG. 13 illustrates an experimental protocol for evaluating the efficacy of a *Streptococcus pyogenes* culture broth (SP CM>100 kDa) in a cancer cell-transplanted mouse tumor model.

To evaluate the efficacy of SP CM>100 kDa in a cancer cell-transplanted mouse tumor model, an experiment was carried out using the method illustrated in FIG. 13 as follows.

6-week-old female BALB/c mice were grouped into 6 mice per cage and placed in cages without discrimination, and after an acclimatization period of 2 days, mouse cancer cells (CT26) were subcutaneously injected ($1 \times 10^5$ cells/mouse) into the right side of the back of each mouse after day 1. A group for evaluating the efficacy of SP CM>100 kDa was intraperitoneally administered 200 μl of the SP CM>100 kDa produced using the method of Example 2 at 8-hour intervals every day. To evaluate anticancer efficacy, the size (length×width$^2$/2) of tumor tissue was measured at 3-day intervals after injection of cancer cells, and on the next day after the final administration of SP CM>100 kDa (after 28 days), the mice were dissected to collect and observe tumor tissue.

Figure 14A:
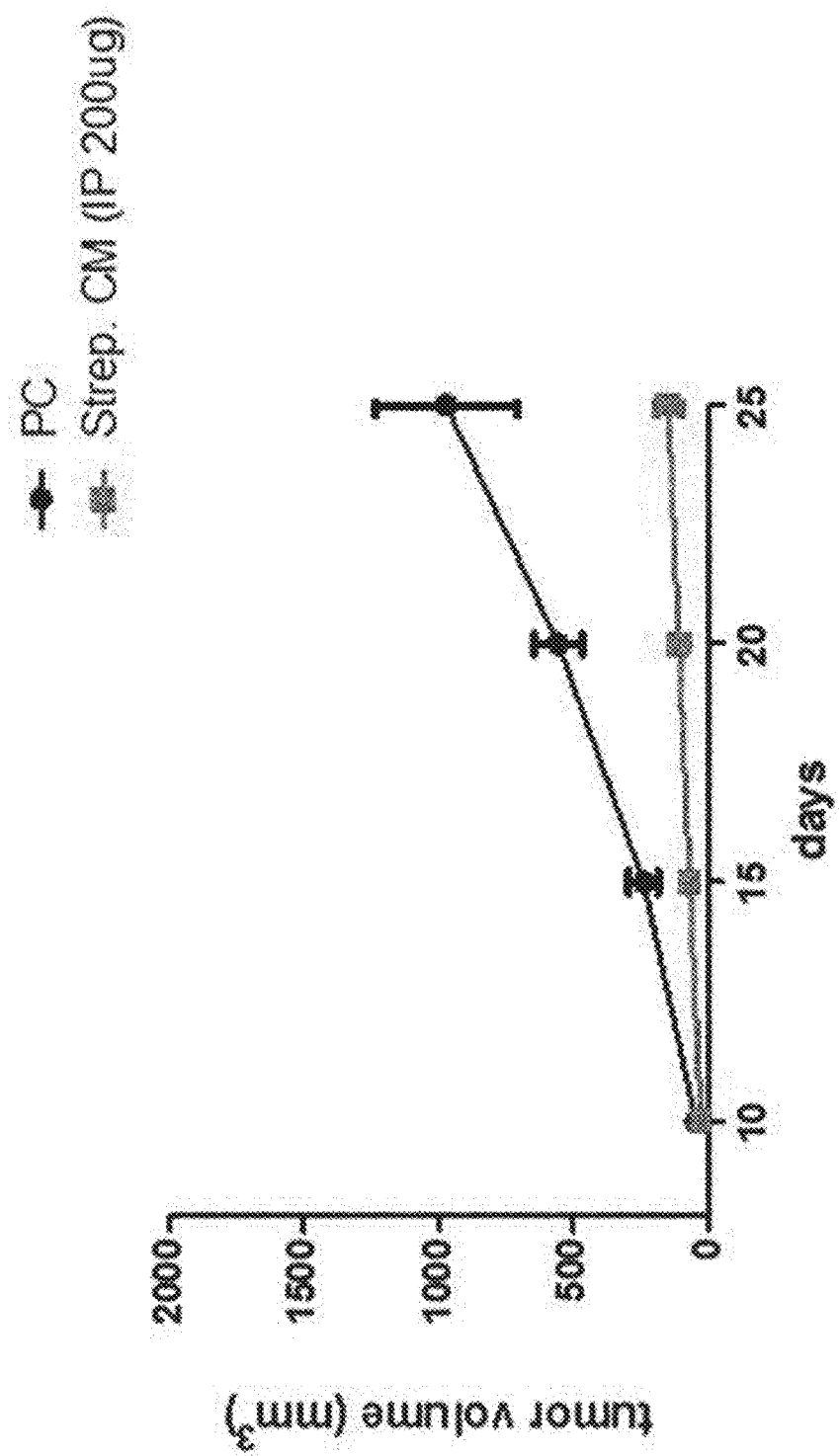
FIG. 14A illustrates the results of evaluating the growth rate of tumor tissue in a cancer cell-transplanted mouse tumor model.
Figure 14B:
FIG. 14B illustrates the results of evaluating the volume of tumor tissue in a cancer cell-transplanted mouse tumor model.

As a result of observing the growth extent and final size of tumor tissue in the SP CM>100 kDa-administered group according to the above method, it was confirmed that the growth rate of tumor tissue was significantly reduced in the case of administering SP CM>100 kDa to the cancer cell-transplanted mouse tumor model, compared to a positive control (P. C, PBS 200 μl) (see FIG. 14A), and it was finally evaluated that the size of tumor tissue was small (see FIG. 14B).

The above results mean that SP CM>100 kDa has an anticancer effect in a colon cancer cell-transplanted mouse tumor model.

Figure 15:
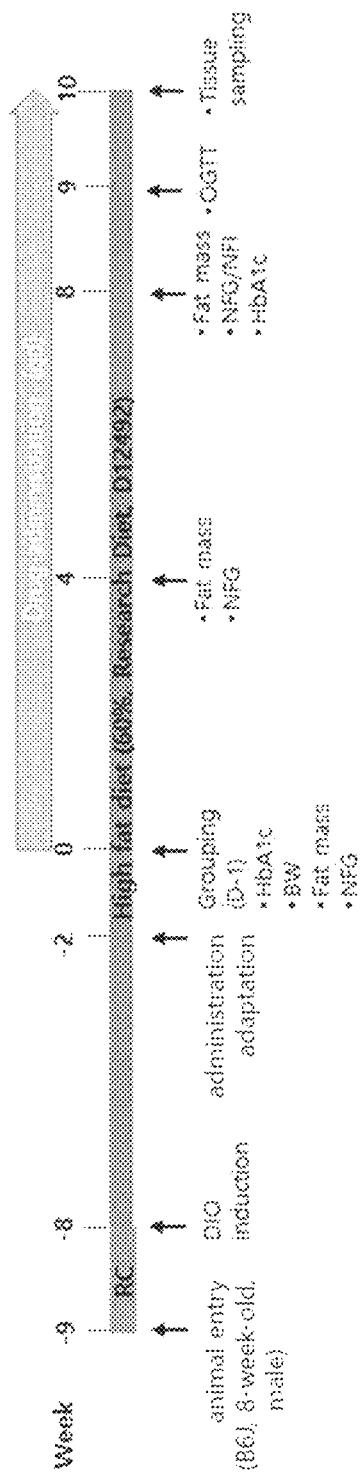
FIG. 15 depicts a protocol for evaluating the efficacy of a *Streptococcus pyogenes* culture broth (SP CM>100 kDa) in a high-fat-diet-induced obesity mouse model.

Example 10 Anti-Obesity and Fatty Liver Improvement Effects of SP CM>100 kDa in High-Fat-Diet-Induced Metabolic Disease Mouse Model To evaluate the efficacy of SP CM>100 kDa in a high-fat-diet-induced metabolic disease mouse model, an experiment was carried out using the method illustrated in FIG. 15 as follows.

8-week-old male C57BL/6 mice were grouped into 10 mice per cage and placed in cages without discrimination, and after an acclimatization period of 7 days, the mice were fed a high fat diet for 8 weeks to induce obesity. A group for evaluating the efficacy of SP CM>100 kDa was orally administered 200 μl of the SP CM>100 kD produced using the method of Example 2 while maintaining a high fat diet from 8 weeks for 10 weeks by using a sonde (rod for oral administration) at 24-hour intervals once a day, and after 10 weeks, the body weight of each mouse was measured, and blood was collected from each mouse to measure ALT, AST, and the like, which are liver function indices. A negative control (con (−)) was orally administered 200 μl of PBS, and a positive control (con(+)) was orally administered 300 mpk of metformin-HCl.

Figure 16:
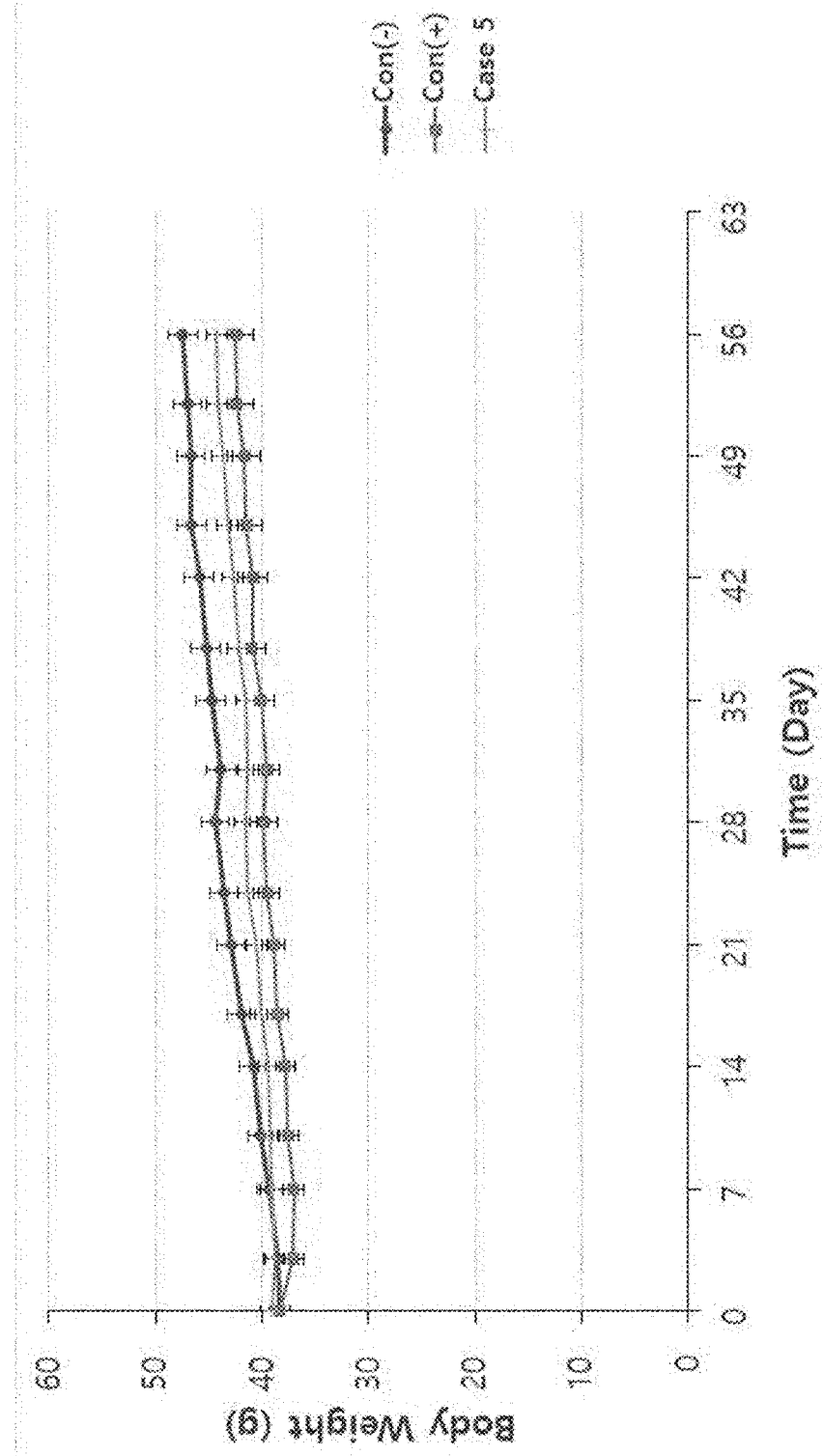
FIG. 16 illustrates the results of evaluating the anti-obesity efficacy of a *Streptococcus pyogenes* culture broth (SP CM>100 kDa) by observing a change in body weight in a high-fat-diet-induced obesity mouse model.
Figure 17:
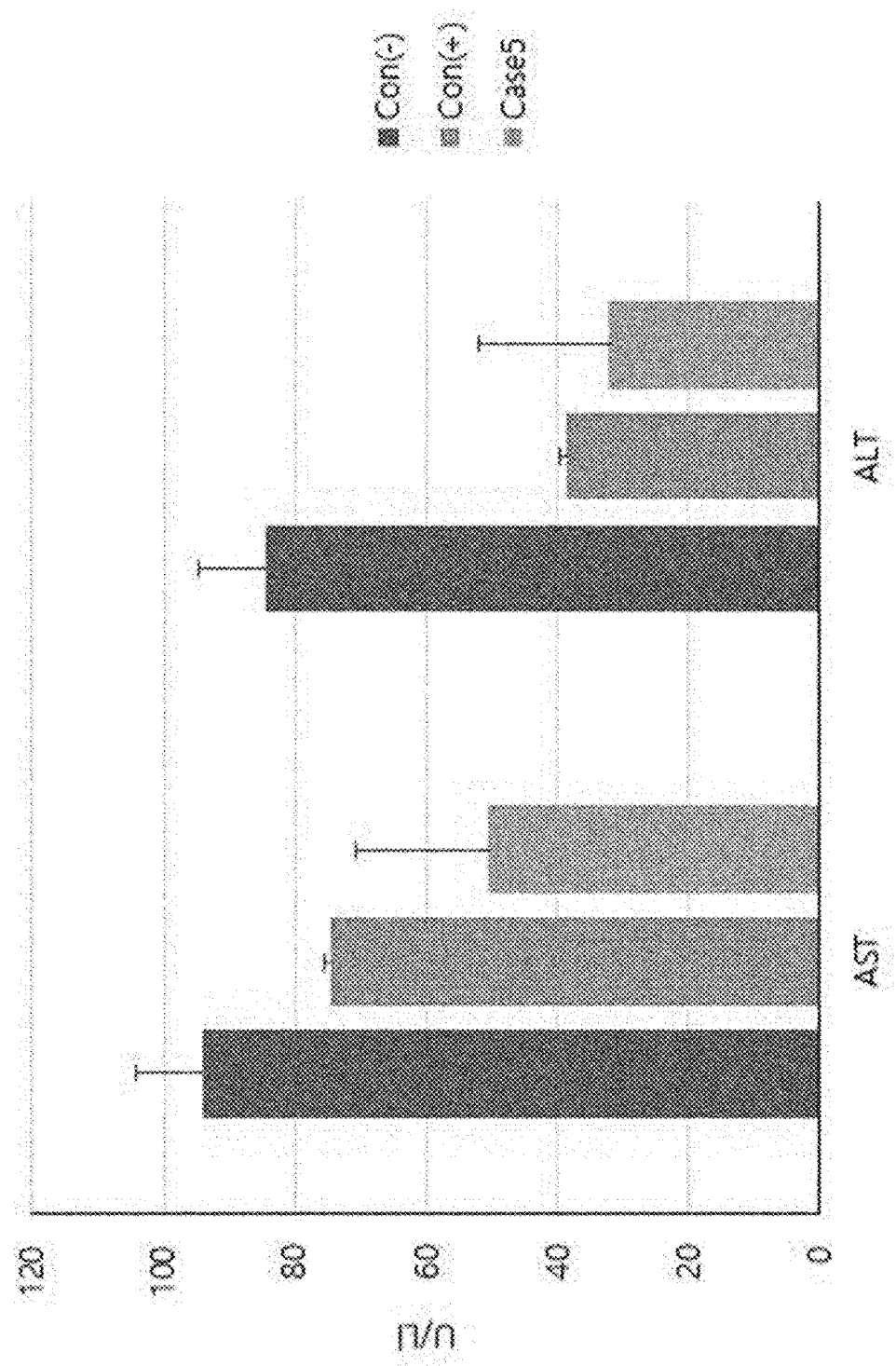
FIG. 17 illustrates the results of evaluating the efficacy of a *Streptococcus pyogenes* culture broth (SP CM>100 kDa) on treating steatosis by analyzing the alanine aminotransferase (ALT) and arspartate aminotransferase (AST) in blood in a high-fat-diet-induced obesity mouse model.

As a result of analyzing the body weight (see FIG. 16) and blood ALT and AST (see FIG. 17) of each mouse in the high-fat-diet-induced metabolic disease model (case 5) administered SP CM>100 kDa for 10 weeks according to the above method, a significant reduction in body weight and significant reductions in blood AST and ALT levels were exhibited in the case of administering SP CM>100 kDa to the high-fat-diet-induced metabolic disease mouse model, compared with the controls.

The above results mean that SP CM>100 kDa inhibits obesity and has a liver function improvement effect in a high-fat-diet-induced metabolic disease mouse model.

The above-described description of the present invention is provided for illustrative purposes, and those of ordinary skill in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

The inventors of the present invention confirmed that a *Streptococcus pyogenes* culture broth or a protein isolated from the culture broth exhibited an anti-inflammatory effect when an inflammatory disease model was treated therewith, and thus the *Streptococcus pyogenes* culture broth or the protein isolated from the culture broth according to the present invention can be effectively used to develop a drug, a health functional food, an inhalant, a cosmetic composition, or the like for preventing inflammatory diseases, metabolic diseases, and cancer, or alleviating or treating symptoms thereof, thus being industrially applicable.

The invention claimed is:

1. A method of treating or alleviating cancer, comprising administering to a subject in need thereof a composition comprising an effective amount of a *Streptococcus pyogenes* culture broth or a protein isolated from the culture broth,
   wherein the culture broth or the protein isolated from the culture broth is produced by centrifuging a liquid medium containing *Streptococcus pyogenes* and collecting a supernatant excluding *Streptococcus pyogenes* cells, and wherein the protein has a molecular weight of 100 kDa or more, and
   wherein the cancer is one or more selected from the group consisting of lung cancer, laryngeal cancer, oral cancer, gastric cancer, colon-rectal cancer, liver cancer, cholangiocarcinoma, pancreatic cancer, breast cancer, ovarian cancer, cervical cancer, kidney cancer, bladder cancer, prostate cancer, brain tumors, leukemia, and lymphoma.

2. The method of claim 1, wherein the composition inhibits an inflammatory cytokine.

3. The method of claim 2, wherein the inflammatory cytokine is interleukin-8.

4. The method of claim 1, wherein the composition is pharmaceutical composition or food composition.

5. A method of treating or alleviating cancer, the method comprising the steps of:
   a) centrifuging a liquid medium containing *Streptococcus pyogenes* to obtain a centrifuged supernatant;
   b) collecting the supernatant excluding *Streptococcus pyogenes* cells; and
   c) administering to a subject in need thereof an effective amount of the supernatant or the protein isolated from the supernatant,
   wherein the protein has a molecular weight of 100 kDa or more, and
   wherein the cancer is one or more selected from the group consisting of lung cancer, laryngeal cancer, oral cancer, gastric cancer, colon-rectal cancer, liver cancer, cholangiocarcinoma, pancreatic cancer, breast cancer, ovarian cancer, cervical cancer, kidney cancer, bladder cancer, prostate cancer, brain tumors, leukemia, and lymphoma.

* * * * *